US007432419B2

(12) United States Patent
Gupta

(10) Patent No.: US 7,432,419 B2
(45) Date of Patent: Oct. 7, 2008

(54) COMPOSITIONS AND METHODS FOR THE TREATMENT OF PIERCE'S DISEASE

(75) Inventor: Goutam Gupta, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 0 days.

(21) Appl. No.: 10/846,172

(22) Filed: May 14, 2004

(65) Prior Publication Data

US 2005/0257285 A1    Nov. 17, 2005

(51) Int. Cl.
    *C12P 21/02*    (2006.01)
(52) U.S. Cl. ............. 800/302; 435/69.1; 435/252.33; 435/320.1; 435/419; 435/348; 530/350; 536/23.5
(58) Field of Classification Search ............. 536/23.1, 536/23.4, 24.2; 530/350; 435/468, 69.7
    See application file for complete search history.

(56) References Cited

U.S. PATENT DOCUMENTS

2004/0052814 A1 *    3/2004    Shi et al. ............. 424/190.1

OTHER PUBLICATIONS

Weng et al. Cloning and expression of the cecropin B thanatin hybrid antimicriobial peptided in *E. coli* Chinese journal of biotechnology May 2002 18(3) pp. 352-355.*
Shin et al. Structure-antibacterial antitumor and hemolytic activity relations hips of cecropin A -magainin2 and Cecropim A-melittin hybrid peptides Journal of Peptide Research 1999 53(1) 82-90, abstract only.*
Accession No. AAP80335 1990.*
Boman, 2003, J. Int. Med. 254: 197-215.
Raj & Dentino, 2002, FEMS Microbiol. Lett. 206: 9.
Hancock, 2001, The LANCET 1: 156.
Davis et al., 1978, Science 199: 75-77.
Chang et al., 1993, Curr. Microbiol. 27: 137-142.
Goheen et al., 1973, Phytopathology 63: 341-345.
Hopkins, 1989, Annu. Rev. Phytopathol. 27: 271-290.
Wells et al., 1983, Phytopathology 73: 859-862.
De Lima, et al., 1996, Fitopatologia Brasileira 21(3).
Purcell and Saunders, 1999, Plant Dis. 83: 825-830.
Hendson, et al., 2001, Appl. Environ. Microbiol 67: 895-903.
Purcell and Hopkins, 1996, Annu. Rev. Phytopathol. 34: 131-151.
Briansky et al., 1983, Phytopathology 73: 530-535.
Purcell et al., 1979, Science 206: 839-841).
Hill and Purcell, 1997, Phytopathology 87: 1197-1201.
Garcia et al., 1998, Infection and Immunity 66:1408-12.
Lusitani et al., 2002, J. Infect. Dis. 185: 797-804.
Miyasaki and Bodeau, 1991, Infection and Immunity 59: 3015-20.
Breuning et al., 2002, Proceedings, Pierce's Disease Research Symposium, Eds. Athar-Tariq et al., San Diego, CA.
Epand and Vogel, 1999, Biochimica Biophysica Acta 1462: 11-28.
Bechinger, 1997, J. Membrane Biol. 156: 197-211.
Hong et al., 2003, Antimicrobial Agents Chemother. 47: 1-6.
Broekaert et al., 1997, Crit. Rev. Plant Sci. 16: 297-323.
Bonmatin et al., 1992, J. Biomol. NMR 2: 235-256.
Fehlbaum et al., 1994, J. Biol. Chem. 269: 33159-33163.
Thomma et al., 2003, Planta 216: 193-202.
Segura et al., 1998, FEBS Letters 435: 159-162.
Boman et al., 1991, Cell 65: 205-207.
Boman et al., 1991, Eur. J. Biochem. 201: 23-31.
Wade et al., 1990, Proc. Natl. Acad. Sci. USA 87: 4761-4765.
Vaara and Vaara,1994, Antimicrobial Agents Chemother 38:2498-2501.
Mason et al., 1996, Proc. Natl. Acad. Sci. USA 93: 5335-5340.
Decendit et al., 1996, Biotechnol. Lett. 18: 659-662.
Szankowski et al., 2003 Plant Cell Rep. 22: 141-149.
Hiatt et al., 1989, Nature 342: 76-78.
Kumagai et al., 1993, Proc. Natl. Acad. Sci. USA 90: 427-430.
Verch et al., 2004, Cancer Immunol. Immunother. 53: 92-99.
Verch et al., 1998, J. Immunol. Methods 220: 69-75.
Pieters, 2001, Current Opinion Immunol. 13:37-44.
Baquero and Blazquez, 1997, Trends Ecol. Evol. 12:482-487.
Sharma v. Surolia, 1997, Journal of Molecular Biology 267: 433-445.
Barre et al., 2001, Biochimie 83:645-651.
Feinberg et al., 2001, Science 294: 2163-2167.
Rep et al., 2003, FEBS Letters 534:82-86.
Peschel, 2002, Trends Microbiol. 10:179.
Belmonte, US Patent Application 20030004065.
Meredith et al., 2003, Proceedings of the 2003 Pierce's Disease Research Symposium, Calif. Dept. Food & Agriculture, p. 23-25.

\* cited by examiner

*Primary Examiner*—James Ketter
(74) *Attorney, Agent, or Firm*—Kenneth K. Sharples

(57) ABSTRACT

Chimeric anti-microbial proteins, compositions, and methods for the therapeutic and prophylactic treatment of plant diseases caused by the bacterial pathogen *Xylella fastidiosa* are provided. The anti-microbial proteins of the invention generally comprise a surface recognition domain polypeptide, capable of binding to a bacterial membrane component, fused to a bacterial lysis domain polypeptide, capable of affecting lysis or rupture of the bacterial membrane, typically via a fused polypeptide linker. In particular, methods and compositions for the treatment or prevention of Pierce's disease of grapevines are provided. Methods for the generation of transgenic *Vitus vinefera* plants expressing xylem-secreted anti-microbial chimeras are also provided.

18 Claims, 9 Drawing Sheets

(2 of 9 Drawing Sheet(s) Filed in Color)

A

B

C

A

B 1        2

A

B

COMPOSITIONS AND METHODS FOR THE TREATMENT OF PIERCE'S DISEASE

STATEMENT REGARDING GOVERNMENT RIGHTS

This invention was made with government support under grant number DE-FG02-98ER62647 from the United States Department of Energy and Contract No. W-7405-ENG-36 awarded by the United States Department of Energy to The Regents of The University of California. The government has certain rights in this invention.

FIELD OF THE INVENTION

This invention relates to the treatment of plant diseases caused by the xylem-limited bacteria *Xylella fastidiosa* (Xf), such as Pierce's Disease of grapevine.

BACKGROUND OF THE INVENTION

Antibiotics are commonly used to target specific genes of both gram-positive and gram-negative bacteria and clear them before they can cause physiological damage. However, over the last two decades, the widespread use of certain antibiotics have led to antibiotic resistance in the target microbial genes, thereby severely limiting their clinical use (Peschel, 2002, Trends Microbiol. 10:179). The clinical world witnessed an alarming trend in which several gram-positive and gram-negative have become increasingly resistant to commonly used antibiotics, such as penicillin and vancomycin, which target the enzymes involved in the formation and integrity of bacterial outer membrane.

The discovery of linear anti-microbial proteins, such as the insect cecropins, and disulfide-bridged anti-microbial proteins, such as the defensins, initially raised hopes in anti-microbial therapy. Both cecropins and defensins have been evolutionarily conserved in invertebrates and vertebrates and constitute a major component of host innate immune defense (Boman, 2003, J. Int. Med. 254: 197-215; Raj & Dentino, FEMS Microbiol. Lett., 202, 9, 2002; Hancock The LANCET 1, 156, 201). Members of the cecropin and defensin families have been isolated from plants, insects, and mammals. They are normally stored in the cytoplasmic granules of plant, insect, and human cells and undergo release at the site of pathogen attack. Rather than targeting a specific enzyme, positively charged anti-microbial peptides interact with the negatively charged (and somewhat conserved) membrane components, i.e., membrane peptidoglycan (PGN) in gram-positive bacteria and lippopolysaccharide (LPS) in gram-negative bacteria.

Following the identification and initial characterization of the cecropins and defensins, it was anticipated that these peptides would not be subject to microbial resistance. However, it was soon discovered that both gram-positive and gram-negative bacteria can develop resistance against these anti-microbial proteins by modifying their membrane glycolipid components. These modifications probably weaken the initial interaction of these anti-microbial peptides with the membrane glycolipid and thereby significantly reduce their ability to form pores and lyse bacterial membrane.

Globally, one-fifth of potential crop yield is lost due plant diseases, primarily as a result of bacterial pathogens. *Xylella fastidiosa* (Xf) is a devastating bacterial pathogen that causes Pierce's Disease in grapevines (Davis et al., 1978, Science 199: 75-77), citrus variegated chlorosis (Chang et al., 1993, Curr. Microbiol. 27: 137-142), alfalfa dwarf disease (Goheen et al., 1973, Phytopathology 63: 341-345), and leaf scorch disease or dwarf syndromes in numerous other agriculturally significant plants, including almonds, coffee, and peach (Hopkins, 1989, Annu. Rev. Phytopathol. 27: 271-290; Wells et al., 1983, Phytopathology 73: 859-862; De Lima, et al., 1996, Fitopatologia Brasileira 21(3)). Although many agriculturally important plants are susceptible to diseases caused by Xf, in the majority of plants Xf behaves as a harmless endophyte (Purcell and Saunders, 1999, Plant Dis. 83: 825-830). Strains of Xf are genetically diverse and pathogenically specialized (Hendson, et al., 2001, Appl. Environ. Microbiol 67: 895-903). For example, certain strains cause disease in specific plants, while not in others. Additionally, some strains will colonize a host plant without causing the disease that a different Xf strain causes in the same plant.

Xf is acquired and transmitted to plants by leafhoppers of the Cicadellidae family and spittlebugs of the Cercropidae family (Purcell and Hopkins, 1996, Annu. Rev. Phytopathol. 34: 131-151). Once acquired by these insect vectors, Xf colonies form a biofilm of poorly attached Xf cells inside the insect foregut (Briansky et al., 1983, Phytopathology 73: 530-535; Purcell et al., 1979, Science 206: 839-841). Thereafter, the insect vector remains a host for Xf propagation and a source of transmission to plants (Hill and Purcell, 1997, Phytopathology 87: 1197-1201). In susceptible plants, Xf multiplies and spreads from the inoculation site into the xylem network, where it forms colonies that eventually occlude xylem vessels, blocking water transport.

Pierce's disease is an Xf-caused lethal disease of grapevines in North America through Central America, and has been reported in parts of northwestern South America. It is present in some California vineyards annually, and causes the most severe crop losses in Napa Valley and parts of the Central Valley. Pierce's Disease is efficiently transmitted by the glassy-winged sharpshooter insect vector. In California, the glassy-winged sharpshooter is expected to spread north into the citrus belt of the Central Valley and probably will become a permanent part of various habitats throughout northern California. It feeds and reproduces on a wide variety of trees, woody ornamentals and annuals in its region of origin, the southeastern United States. Crepe myrtle and sumac are especially preferred. It reproduces on Eucalyptus and coast live oaks in southern California.

Over the years, a great deal of effort has been focused on using insecticides to localize and eliminate the spread of this disease. However, there remains no effective treatment for Pierce's Disease. Other crops found in these regions of the State of California have also been effected, including the almond and oleander crops. The California Farm Bureau reports that there were 13 California counties infested with the glassy-winged sharpshooter in the year 2000, and that the threat to the State of California is $14 billion in crops, jobs, residential plants and trees, native plants, trees and habitats.

SUMMARY OF THE INVENTION

The invention relates to chimeric anti-microbial proteins (CHAMPs) designed to target gram-positive and gram negative bacterial pathogens. The chimeric anti-microbial proteins of the invention combine proteins derived from two evolutionarily conserved arms of innate host immunity, and circumvent the development of resistance commonly seen with antibiotic therapies by targeting the final carbohydrate and lipid products on the pathogen cell membrane, rather than targeting one or more of the many enzymes involved in the synthesis of these bacterial membrane components.

In one aspect, the invention is directed to the treatment of Pierce's Disease, as well as a number of related plant diseases caused by the infiltration of *Xylella fastidiosa* colonies into the xylem chambers of the affected plant, using CHAMPs designed to bind to and lyse Xf. The invention provides chimeric anti-microbial proteins against Xf, comprising a surface recognition domain capable of binding to the Xf bacterial cell membrane or a component thereof, physically linked to an anti-microbial peptide acting as a bacterial lysis domain. The anti-Xf chimeras more effectively kill the target bacteria by increasing the concentration of a protein with antimicrobial activity through physical association with a high affinity binding component (the surface recognition domain). Higher concentrations of the antimicrobial peptide results in greater aggregation and insertion into the bacterial membrane, thereby increasing the formation of pores therein, and ultimately accelerating bacterial cell lysis.

In particular, chimeric anti-microbial proteins comprising a surface recognition domain physically linked to an insect cecropin or a plant group IV defensin are provided. In one embodiment, the surface recognition domain is human neutrophil elastase (HNE), or an active fragment thereof, and the insect cecropin is cecropin A or cecropin B. In another embodiment, the surface recognition domain is HNE, or an active fragment thereof, and the plant defensin is spinach group IV defensin. In preferred embodiments, the HNE and cecropin or defensin components are physically linked by a fused polypeptide linker of between 2 and 20 amino acids.

The invention also provides isolated nucleic acid molecules encoding the anti-microbial chimeras of the invention, expression vectors comprising such nucleic acid molecules, and cells comprising such expression vectors. Methods for producing the chimeras of the invention are provided, and generally comprise providing an expression vector which contains an expressible construct encoding the chimera, transforming or transfecting a suitable host cell with the expression vector, and expressing the chimera encoded by the expression vector.

Transgenic plants expressing chimera of the invention are also provided. Therapeutic and prophylactic strategies for the treatment of plant diseases caused by Xf infection, such as Pierce's Disease of grape plants, are also provided.

STATEMENT REGARDING COLOR DRAWINGS

This patent or application file contains at least one drawing executed in color. Copies of this patent or patent application publication with color drawings will be provided by the United States Patent and Trademark Office upon request and payment of the necessary fee.

DETAILED DESCRIPTION OF THE INVENTION

Figure 1:
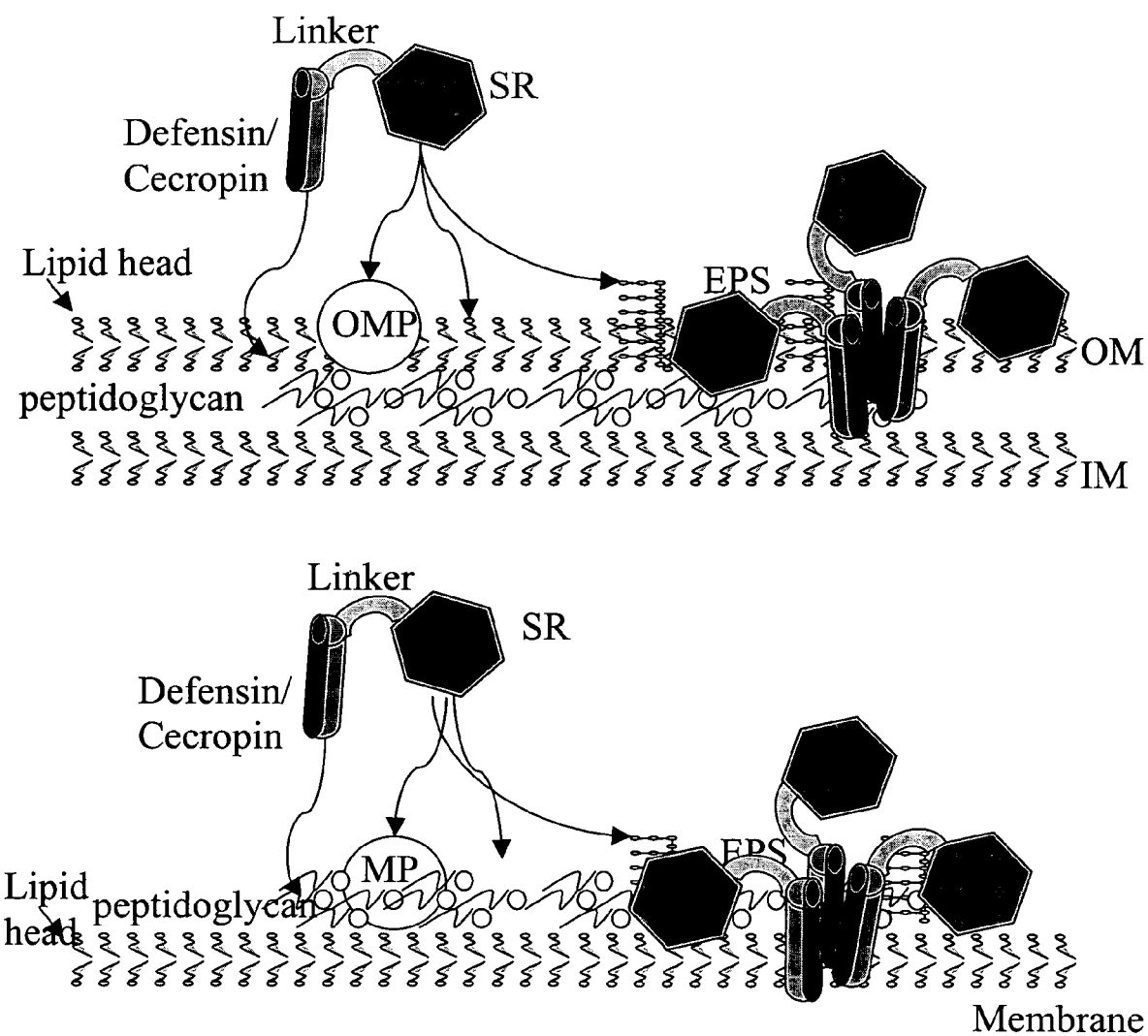
FIG. 1. Schematic diagrams showing anti-microbial chimeric protein designs and interaction with bacterial membrane components in (A) gram-negative bacteria, and (B) gram-positive bacteria. Abbreviations: EPS=extracellular polysaccharides; OM=outer membrane in gram-negative bacteria; IM=inner membrane in gram-positive bacteria; OMP=outer membrane protein; MP=membrane protein.
Figure 2:
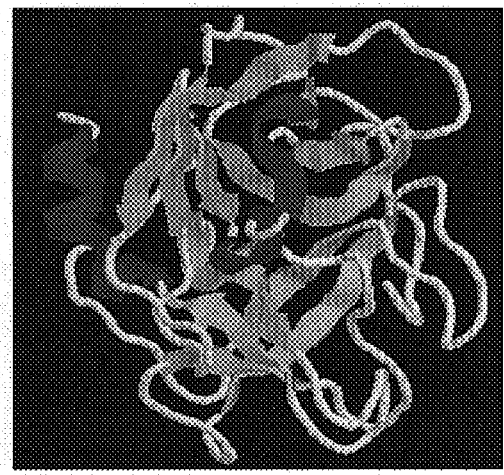
FIG. 2. Three-dimensional structural renderings of (A) human neutrophil elastase (the N-terminus indicated by cyan colored arrow), (B) plant defensin Ah-Amp1, and (C) cecropin A(1-8)-magainin 2(1-12) hybrid peptide.
Figure 2:
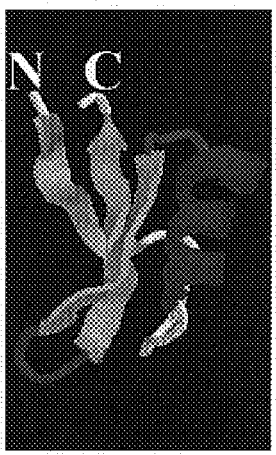
Figure 2:
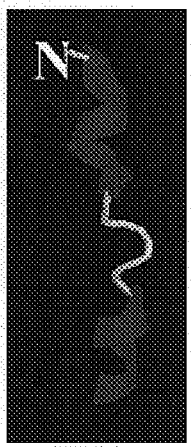

Definitions:

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

The term "surface recognition domain", or "SRD", refers to a polypeptide which is capable of binding to a component of a bacterial membrane. For example, in the case of gram-negative bacteria, an SRD may recognize, bind or associate with an outer membrane protein (e.g., MopB on the surface of Xf and *E. coli*), a carbohydrate component of the bacterial membrane, or extracellular polysaccharides. In the case of gram-positive bacteria, an SRD may, for example, recognize, bind or associate with a bacterial membrane protein, extracellular polysaccharide, or peptidoglycan components.

The term "bacterial lysis domain" refers to a polypeptide which is capable of affecting lysis or rupture of the bacterial membrane when present at the bacterial membrane surface, typically through some bacterial membrane-invasive action, including without limitation pore formation, channel formation, folding-insertion reactions, and complete structural disruptions. Such polypeptides include without limitation the cecropin and defensin proteins, including both native mature proteins and polypeptide fragments retaining such lytic activity.

The terms "chimera", "anti-microbial chimera", "anti-microbial chimeric protein", and "CHAMP" are used interchangeably and refer to heterologous polypeptides comprising a surface recognition domain and a lysis domain which are physically linked.

"Physical linkage" refers to any method known in the art for functionally connecting two molecules (which are termed "physically linked"), including without limitation, recombinant fusion with or without intervening domains, intein-mediated fusion, non-covalent association, covalent bonding (e.g., disulfide bonding and other covalent bonding), hydrogen bonding; electrostatic bonding; and conformational bonding, e.g., antibody-antigen, and biotin-avidin associations.

As used herein, "linker" refers to a molecule or group of molecules that connects two molecules, such as SRD and lysis domains, and serves to place the two molecules in a preferred configuration.

A "Coiled-coil" as used herein refers to an α-helical oligomerization domain found in a variety of proteins. Proteins with heterologous domains joined by coiled coils are described in U.S. Pat. Nos. 5,716,805 and 5,837,816. Structural features of coiled-coils are described in Litowski and Hodges, 2002, J. Biol. Chem. 277:37272-27279; Lupas, 1996, TIBS 21:375-382; Kohn and Hodges, 1998, TIBTECH 16: 379-389; and Müller et al., 2000, Methods Enzymol. 328: 261-282. Coiled-coils generally comprise two to five α-helices (see, e.g., Litowski and Hodges, 2002, supra). The α-helices may be the same or difference and may be parallel or anti-parallel. Typically, coiled-coils comprise an amino acid heptad repeat: "abcdefg."

"Fused" refers to linkage by covalent bonding.

A "fusion protein" refers to a chimeric molecule formed by the joining of two or more polypeptides through a bond formed one polypeptide and another polypeptide. Fusion proteins may also contain a linker polypeptide in between the constituent polypeptides of the fusion protein. The term "fusion construct" or "fusion protein construct" is generally meant to refer to a polynucleotide encoding a fusion protein.

The term "heterologous" when used with reference to a nucleic acid or polypeptide indicates that the nucleic acid or polypeptide comprises two or more subsequences that are not found in the same relationship to each other in nature. For instance, a nucleic acid is typically recombinantly produced, having two or more sequences from unrelated genes arranged to make a new functional nucleic acid. Similarly, a heterologous protein indicates that the protein comprises two or more subsequences that are not found in the same relationship to each other in nature (e.g., a chimeric protein).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "peptidomimetic" and "mimetic" refer to a synthetic chemical compound that has substantially the same structural and functional characteristics of the polypeptides of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *J. Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of, e.g., —CH2NH—, —CH2S—, —CH2—CH2—, —CH=CH— (cis and trans), —COCH2—, —CH(OH)CH2—, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Such conservatively modified variants are in addition to and do not exclude polymorphic variants, interspecies homologs, and alleles of the invention.

For example, substitutions may be made wherein an aliphatic amino acid (G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, E or D, may be substituted with its uncharged counterpart, Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the compliment of a test sequence. Preferably, the identity exists over a region that is at least about 22 amino acids or nucleotides in length, or more preferably over a region that is 30, 40, or 50-100 amino acids or nucleotides in length.

The term "similarity," or percent "similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 98% or 99% similar over a specified region or, when not specified, over the entire sequence), when compared and aligned for maximum correspondence over a comparison window, or designated region as measured using one of the following sequence comparison algorithms or by manual alignment and visual inspection. Such sequences are then said to be "substantially similar."

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). Typically, the Smith & Waterman alignment with the default parameters are used for the purposes of this invention Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, typically with the default parameters described herein, to determine percent sequence identity for the nucleic acids and proteins of the invention.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. The default parameters of BLAST are also often employed to determined percent identity or percent similarity.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

Anti-Microbial Chimeric Protein Design:

Pore formation within the bacterial membrane by anti-microbial proteins is a concentration driven process mediated by their aggregation in the bacterial membrane. The invention is based, in part, on the hypothesis that the probability of pore formation, and therefore lytic activity, may be enhanced by improving the initial interaction between the anti-microbial protein and the bacterial membrane. Towards this end, the invention's anti-microbial strategy aims at joining a membrane surface recognition domain (SRD), typically by a flexible polypeptide linker, to an anti-microbial protein or active fragment thereof (bacterial lysis domain). Instead of targeting the enzymes involved in metabolic pathways, like current antibiotic therapy methods, such chimeric anti-microbial proteins target the invariant lipid, carbohydrate, and protein components of the bacterial membrane with the aid of two functional domains.

The anti-microbial chimeric proteins of the invention generally share a common structural organization, comprising the unit A-X-B, where component A represents an SRD; component X represents a physical linker, and component B represents a bacterial lysis domain. Schematic illustrations of anti-microbial chimeras and their interaction with various bacterial membrane components are shown in FIG. 1. The SRD and bacterial lysis domain are also referred to as the "active" components of the chimeras of the invention.

Using various molecular evolution and mutation techniques, the effective therapeutic range of an anti-microbial chimera of the invention (or the active components thereof) may be modified, for the purpose of increasing affinity, increasing killing effect, broadening the target bacteria range, improving targeting characteristics, and the like. Such methods may also be employed to improve folding and solubility characteristics of a chimera of the invention. For example, the methods described in co-pending, co-owned U.S. patent application Ser. No. 10/423,463, filed Apr. 24, 2003, may be employed for the directed evolution of chimera or the individual components thereof.

Surface Recognition Domain:

The surface recognition domain of a chimera of the invention may be selected from a variety of known proteins which have affinity for various components of the bacterial membrane. In the design of CHAMPs against gram-negative bacteria, the SRD is preferably selected or designed to target an abundant and conserved outer membrane protein, carbohydrate moieties associated with membrane lippopolysaccharide, or extracellular polysaccharide. In the design of CHAMPs against gram-positive bacteria, the SRD is preferably selected or designed to target an abundant and conserved membrane protein, peptidoglycan or extracellular polysaccharide.

A SRD targeting a membrane protein may be, for example, a high-affinity ligand which binds to the membrane protein (e.g., specific antibody) or an enzyme that cleaves the protein. An SRD targeting a carbohydrate moiety may be derived from the carbohydrate recognition domains (CRD) of lectins, which show a broad repertoire of specificity. Selection of an appropriate SRD may be used to facilitate specific bacterium targeting or broad spectrum targeting.

One SRD useful in the construction of CHAMPs against gram-negative bacterial is elastase. In one embodiment, a CHAMP designed to kill the plant pathogen *Xylella fastidiosa* incorporates human neutrophil elastase (HNE), or active fragment thereof (i.e, truncated HNE; SEQ ID NO: 1), as its SRD component (see Example 1, infra). Recent research has shown that human neutrophil elastase can kill the causative agent of Lyme Disease, *Borrelia burgdorferi* (Garcia et al., 1998, Infection and Immunity 66:1408-12; Lusitani et al., 2002, J. Infect. Dis. 185: 797-804). Additionally, elastase can augment the cidal properties of other anti-microbial proteins, such as the antimicrobial granule protein Azurocidin, which shows increased cidal activity in the presence of elastase (Miyasaki and Bodeau, 1991, Infection and Immunity 59: 3015-20).

Neutrophil elastase is also known to target outer membrane proteins. In the case of *Xylella fastidiosa*, the outer membrane protein mopB is abundant on the surface of the cell, and appears to be the major outer membrane protein of Xf, most likely involved in xylem binding (Breuning et al., 2002, Proceedings, Pierce's Disease Research Symposium, Eds. Athar-Tariq et al., San Diego, Calif.). Applicants' sequence-structure analysis of mopB have identified surface-exposed elastase-specific cleavage sites. Additionally, preliminary results demonstrate that purified mopB is at least partially digested by human neutrophil elastase (see FIG. 8), providing evidence that mopB is targeted by HNE. Finally, the results shown in FIG. 3 (see also, Example 2), indicate that elastase greatly enhances Cecropin B-stimulated lysis of Xf cells.

In the design of an SRD component of a chimera of the invention, both full length proteins and active fragments thereof may be utilized. In the case of elastase, an active fragment that retains native fold and binding activity may be used. In one specific embodiment, a 219 amino acid fragment of human neutrophil elastase, having the following amino acid sequence (corresponding to residues 29 through 247 of the full length human neutrophil elastase structure), may be used as the SRD in an anti-microbial chimeric protein targeting gram-negative bacteria, such as Xf.

(SEQ ID NO: 1)

EIVGGRRARP HAWPFMVSLQ LRGGHFCGAT LIAPNFVMSA AHCVANVNVR AVRVVLGAHN

LSRREPTRQV FAVQRIFENG YDPVNLLNDI VILQLNGSAT INANVQVAQL PAQGRRLGNG

VQCLAMGWGL LGRNRGIASV LQELNVTVVT SLCRRSNVCT LVRGRQAGVC FGDSGSPLVC

NGLIHGIASF VRGGCASGLY PDAFAPVAQF VNWIDSIIQ

In another embodiment, the entire human neutrophil elastase protein is used as the SRD. The amino acid sequence of full length human neutrophil elastase is provided below.

```
                                                            (SEQ ID NO: 2)
MTLGRRLACL FLACVLPALL LGGTALASEI VGGRRARPHA WPFMVSLQLR GGHFCGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTH
```

Bacterial Lysis Domain:

The bacterial lysis domain of an anti-microbial chimera of the invention may be selected from a variety of known anti-microbial proteins which have an invasive effect on the target bacteria cell membrane, leading to lysis or rupture of the membrane. For example, some antimicrobial peptides aggregate and insert within the bacterial membrane, thereby affecting the formation of pores in the bacterial membrane, which ultimately results in bacterial cell lysis. A large number of antimicrobial peptides are known (for reviews, see Boman, 2003, J. Intern. Med. 254: 197-215; Epand and Vogel, 1999, Biochimica Biophysica Acta 1462: 11-28; Bechinger, 1997, J. Membrane Biol. 156: 197-211).

The cationic nature of antimicrobial peptides promotes their association with bacterial cell membranes, which are anionic. Following such membrane association, the antimicrobial peptides exert activity on membrane components, including ion channel formation, aqueous pore formation, blebbing followed by osmotic rupture, and other non-specific disruptions to membrane integrity or architecture. However, it is not entirely clear whether all antimicrobial peptides exert their killing effect directly through membrane perturbation. In one case, for example, the insect antimicrobial peptide cecropin A effects the transcriptional levels of numerous *E. coli* genes when presented at sublethal doses (Hong et al., 2003, Antimicrobial Agents Chemother. 47: 1-6).

In preferred anti-Xf chimera embodiments, a defensin or a cecropin is used as the bacterial lysis domain of the chimera. Defensins are cysteine rich proteins, and are present in plants, insects, and humans (Broekaert et al., 1997, Crit. Rev. Plant Sci. 16: 297-323; Bonmatin et al., 1992, J. Biomol. NMR 2: 235-256; Feldbaum et al., 1994, J. Biol. Chem. 269: 33159-33163; Thomma et al., 2002, Planta 216: 193-202). Defensin sequence, structure, and activity vary depending on their source. Insect defensins are active primarily on gram-positive bacteria whereas human defensins are active on both gram-positive and gram-negative bacteria.

Until recently, plant defensins were thought to be active only on fungi; however, a recently described novel class of plant defensins isolated from *Spinachia oleracea*, the group IV plant defensins, show strong anti-bacterial activity against both gram-positive and gram-negative bacteria (Segura et al., 1998, FEBS Letters 435: 159-162). In one embodiment, the group IV plant defensin So-D2 is used as the bacterial lysis domain. The amino acid sequence of So-D2 is shown below (Segura et al., supra).

```
                                   (SEQ ID NO: 3)
GIFSSRKCKT PSKTFKGICT RDSNCDTSCR YEGYPAGDCK GIRRRCMCSK PC
```

Various other group IV plant defensins may also be utilized, including without limitation So-D3, So-D4, So-D5, So-D6 and So-D7 (Segura et al., supra).

Cecropins are powerful anti-microbial compounds, and have been isolated from insects and humans (Bowman et al., 1991, Cell 65: 205-207; Bowman et al., 1991, Eur. J. Biochem. 201: 23-31; Wade et al., 1990, Proc. Natl. Acad. Sci. USA 87: 4761-4765). Cecropins are small (35-39 amino acids), strongly cationic, amphipathic proteins with activity against both gram-negative and gram-positive bacteria. Cecropins are 10-30 times more active against *E. coli* and *P. arginosa* than are defensins or magainins, and are a hundred-fold more potent on gram-negative than on gram-positive bacteria. Cecropin B, in particular, is one of the most potent anti-microbial peptides known.

Cecropins cause instantaneous lysis of bacterial cells by destroying the cytoplasmic membrane. In order to reach the cytoplasmic membrane in gram-negative bacteria, the cecropins must first pass through the outer membrane. In the case of cecropin B, it has been shown that the outer membrane of gram-negative bacteria does not present an effective barrier to its action (Vaara and Vaara, 1994, Antimicrobial Agents Chemother 38:2498-2501). Interestingly, the anti-microbial profile of cecropin B resembles that of the quaternary detergents benzalkonium chloride and cetylpyrimidinium chloride, both of which also lyse gram-negative bacteria (Vaara, 1994, supra). Cecropin A exerts potent activity against *E. coli*, and recent studies suggest that it too can penetrate the bacterial outer membrane, but at sub-lethal concentrations apparently without adverse effect to the bacterium (Hong et al., 2003, Antimicrobial Agents Chemother. 47: 1-6).

The selection of a particular antimicrobial protein as the bacterial lysis component of the CHAMP will depend on particular objectives. In some cases, it may be desirable to utilize a protein exhibiting activity against a broad spectrum of related bacteria, while in other cases it may be desirable to utilize a protein exhibiting activity against a specific bacterial species or strain. In one aspect, the chimeric anti-microbial proteins of the invention are targeted against Xf, a gram-negative bacteria. Accordingly, in one preferred embodiment, cecropin B is used as the lysis domain component.

Physical Linker:

In the practice of the invention, the active components of the chimera are physically linked in order to bring both active components within a physical proximity that will permit and facilitate synergistic binding to, association with, or insertion into the bacterial cell membrane or components thereof, while at the same time providing the flexibility necessary to enable both to orient optimally to their membrane targets.

The antimicrobial chimeras of the invention are designed to concentrate antimicrobial activity at the bacterial cell wall target. The invention achieves this aim by attaching a bacterial lysis domain to a surface recognition domain, typically via a flexible polypeptide linker designed to avoid perturbation of the native folds of both of these active components, while also orienting the lysis domain to improve membrane insertion. Appropriately linked SRD and lysis domains can result in synergistic antimicrobial activity, as suggested by the results of the elastase-cecropin study presented in Example 2, infra.

In some embodiments, the physical linker is designed to remain flexible, in order to permit the binding components to move freely and adopt conformations necessary to simultaneously bind to or associate with their individual membrane targets. For example, a polypeptide linker may be fused to both active components. Typically, polypeptide linkers will be between 2 and 20 amino acids long. In one embodiment, a short di-peptide linker with the amino acid sequence RW is used to fuse or link the SRD (elastase) and bacterial lysis (cecropin B) domains. In another embodiment, the SRD and bacterial lysis domains are fused or linked by a longer polypeptide linker, such as GSTAPPA, (positions 268-274 or 275-281 of SEQ ID NO:6), GSTAPPAGSTAPPA (GSTAPPA$_2$) (positions 268-281 of SEQ ID NO:6), or GSTAPPAGSTA (positions 269-278 of SEQ ID NO:7). See Example 1, infra.

In another embodiment, the 15 amino acid polypeptide QASHTCVCEFNCAPL (positions 111-125 of SEQ ID NO:10) is used as a linker (see Example 3, infra). In certain embodiments, the flexible linker is chosen such that the amphipathic defensin/cecropin moieties are able to aggregate through their hydrophobic faces while simultaneously allowing the SRD to functionally interact with its target.

Other amino acid sequences which provide flexibility and physical orientation enabling binding between the active components of the chimera and the target bacterial cell membrane elements may be evaluated as linkers. Preferably, linker polypeptides are devoid of sequences that give rise to stable inter-linker associations and secondary structures may be employed. Typically, such linkers will comprise near-neutral amino acids (i.e., serine, alanine, threonine, valine and/or glycine residues), and will be attached at one end to the N-terminus of one of the binding components and at the other end to the C-terminus of the other binding component. The length and amino acid sequence of such polypeptide linkers should be designed to be non-perturbing to the native folding of the active components of the chimera, while also permitting the simultaneous binding, association, or insertion to the target.

Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. Additionally, polypeptide linkers may be functionalized with a domain that provides a binding domain, an attachment sequence, etc. (see below).

Preferably, the linker polypeptide should be non-perturbing to the conformational stability and solubility of the active components of the chimera. Solubility characteristics of such linkers may be enhanced using, for example, the introduction of charged residues (see, e.g., U.S. Pat. No. 5,990,275). Linkers should also be designed to reduce the potential for linker-mediated aggregation. To reduce linker susceptibility to proteolytic degradation, candidate linkers may be evaluated for stability in the presence of proteolytic enzymes that may be present in the applications in which the switch will be used. One method for reducing the susceptibility to proteolytic degradation involves the incorporation of a Proline residue, preferably adjacent to a charged amino acid (U.S. Pat. No. 5,990,275).

Alternatively, the active components of the chimera may be physically linked by a non covalent linkage, such as coiled coil linkages (see, e.g., Litowski and Hodges, 2002, J. Biol. Chem. 277:37272-27279; Lupas, 1996, TIBS 21:375-382; Kohn and Hodges, 1998, TIBTECH 16: 379-389; and Müller et al., 2000, Methods Enzymol. 328: 261-282)(such as E and K coils, jun and fos coils, A and B coils), natural heterodimeric interacting proteins (such as immunoglobulin CH1 and CL), proteins mutated to be heterodimeric, such as variants of CH3 containing "knobs and holes" (Ridgeway et al., 1996, Protein Engineering 9: 617), or other physical linkages.

Exemplary coiled-coils include E coils and K coils associated 1:1 to form a heterodimer, A coils and B coils associated 1:1 to form a heterodimer, and other leucine zippers. E coils and K coils are described in detail in Litowski and Hodges, supra.

More specifically, one member of a coiled coil binding pair is attached to the N or C terminus of one active component, and the second member of a coiled coil binding pair is attached to the N or C terminus of the other active component. The interaction between the two coiled coils will bring the active components together. Typically, the members of a coiled-coil binding pair will be placed at the ends of a polypeptide linker used to attach the coiled-coil members to each of the binding components. The length of such polypeptide linkers may be varied to achieve the desired distance between the binding components.

A related embodiment adds disulfide linkage functionality to the coiled-coil binding pairs. In this way, covalent bonds may be formed between coiled-coils after their interaction, resulting in a stabilized coiled-coil linkage with a reduced capacity to disassociate. Such functionality may be achieved by the addition of cysteine residues placed, for example, at either the N or C terminus of the coiled-coil binding members, or within a polypeptide linker fusing the active components to the coil domains.

In another embodiment, interacting proteins or interacting domains may be attached to the active components of the chimera in order to provide a physical linkage. For example, the CH1 and CL antibody domains, or variants of CH3 domains which specifically heterodimerize may also be used (e.g., Ridgway et al., 1996, Protein Eng. 9: 617-621; Atwell et al., 1997, J. Mol. Biol. 270: 26-35). As with the use of coiled-coils, linkers that act as spacers are typically employed between the interacting domains and the active components of the chimera.

For some embodiments, it may be desirable to functionalize the linker in order to provide, for example, a means of attaching the chimera to a solid phase. Where polypeptide linkages are utilized, the linker may be designed to contain an amino acid sequence that permits functional attachment to a solid phase (e.g., a HIS tag sequence). The use of such functional tags may also facilitate purification of recombinantly produced chimera (see, for example, the use of a HIS tag in Lehnert et al., 2001, supra). In one embodiment, an N-terminal HIS tag is incorporated into the chimera.

In one embodiment, where X is a flexible polypeptide linker, the linker also contains a sequence of amino acids further enabling the linker to be bound to the substrate (an "anchoring sequence"). The location of such anchoring sequences within the linker should be sufficiently distanced from each of the active components of the chimera so as not to interfere with bacterial cell membrane targeting. Examples of such anchoring sequences include, without limitation, HIS tags (where, e.g., the substrate is functionalized with a metal chelate or cobalt, etc.), the incorporation of cysteine residues (mediating disulfide bridging chemistry), and the use of a biotinylated linker in combination with a substrate functionalized with avidin.

In a specific embodiment, an anti-microbial chimera of the invention is bound to cobalt-functionalized beads or another solid substrate via a HIS element incorporated into a flexible polypeptide linker used to join the active components of the chimera or fused to the N-terminus of the construct. More particularly, the active components are linked to each other with a polypeptide linker containing an intermediate HIS element, thereby permitting the chimera to be bound to a cobalt containing substrate via the linker (e.g., cobalt beads).

A variety of substrate materials are available, including a number of polymer hydrogel materials which are particularly suited to water soluble biomolecules. Hydrogel microbeads may also be used to bind the chimeras of the invention, arrayed in a column or similar vessel, and used to capture target bacteria from samples delivered into or through the column, capillary or similar vessel. Column type arrays may provide certain advantages, such as the ability to pass biological fluids through the column on a continuous basis.

The selection and optimization of an appropriate linker may be conducted empirically. For example, a number of different polypeptide linkers may be joined to the active components of a chimera and screened for binding and affinity in the presence of target bacteria. Alternatively, molecular modeling may be employed to select and/or optimize linkers (e.g., evaluate the impact of mutations within a polypeptide linker within a chimera-cell membrane complex).

Anti-Microbial Chimeric Proteins Against *Xylella fastidiosa*:

The construction and evaluation of a series of anti-Xf chimera is described in the Examples, infra. The amino acid sequences of exemplary chimera are presented below. All of these exemplary chimeras are constructed as fusion proteins consisting of an elastase (as SRD), a polypeptide linker, and either a plant defensin or an insect cecropin.

Truncated HNE-Cecropin B; N- to C-terminus; linker peptide in boldface:

```
                                                            (SEQ ID NO: 4)
IVGGRRARPHAWPFMVSLQLRGGHFCGATLIAPNFVMSAAHCVANVNVRAVRVVLGAHNLSRR

EPTRQVFAVQRIFENGYDPVNLLNDIVILQLNGSATINANVQVAQLPAQGRRLGNGVQCLAMGW

GLLGRNRGIASVLQELNVTVVTSLCRRSNVCTLVRGRQAGVCFGDSGSPLVCNGLIHGIASFVR

GGCASGLYPDAFAPVAQFVNWIDSIIQRW KIFKKIEKMGRNIRDGIVKAGPAIEVLGSAKAIGK
```

Full length HNE-Cecropin B; N- to C-terminus; linker peptide in boldface:

```
                                                            (SEQ ID NO: 5)
MTLGRRLACL FLACVLPALL LGGTALASEI VGGRRARPHA WPFMVSLQLR GGHFCGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTHRW KIFKKIEKMGRNIRDGIVKAGPAIEVLGSAKAIGK
```

Full-length HNE-Defensin (Spinach Group IV); N- to C-terminus; linker peptide in boldface:

```
                                                            (SEQ ID NO: 6)
MTLGRRLACL FLACVLPALL LGGTALASEI VGGRRARPHA WPFMVSLQLR GGHFCGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTH GSTAPPAGSTAPPA GIFSSRKCKT PSKTFKGICT

RDSNCDTSCR YEGYPAGDCK GIRRRCMCSK PC
```

Full-length HNE-Defensin (Spinach Group IV); N- to C-terminus; linker peptide in boldface:

(SEQ ID NO: 7)

```
MTLGRRLACL FLACVLPALL LGGTALASEI VGGRRARPHA WPFMVSLQLR GGHFCGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTH GSTAPPAGSTA GIFSSRKCKT PSKTFKGICT

RDSNCDTSCR YEGYPAGDCK GIRRRCMCSK PC
```

Development of Mutational Variants:

Variants of native or engineered chimera or chimera components may exhibit expanded target specificity and/or enhanced binding affinity or lysis characteristics. Various methods for developing libraries of random mutants, site-directed mutations, and other modifications to peptide structure are well known and may be employed in the practice of this invention in order to develop chimera variants exhibiting improved biological characteristics, such as higher binding affinities, more specificity, greater solubility or stability characteristics in particular environments, and the like.

In one embodiment, for example, the binding affinity of a chimera, an SRD component, or a lysis component may be improved. Methods of measuring binding affinity are well known, and include, for example, surface plasmon resonance analysis and fluorescence activated cell sorting methodologies. In one approach, surface plasmon resonance analysis using the commercially available BIAcore 1000 instrument (Pharmacia) is used. Briefly, the target bacteria, bacterial membrane or integral component thereof, may be immobilized at one or more concentrations. Various concentrations of mutant peptide, for example, are injected into the flow cell and permitted to form complexes with the target. The complexes are then allowed to dissociate, and on- and off-rates are calculated from the resulting association and dissociation curves, corrected for non-specific binding, with their ratio yielding the equilibrium binding constant (Kd). Control experiments, in which the chimera or component thereof are passed over empty sensor chips are conducted for comparison.

Various display systems may be effectively used to generate libraries of mutants, which may be screened for high affinity binders using existing methodology. For example, a yeast display library of chimera designed against a particular bacterial target may be generated using error-prone PCR or similar techniques, expressed on the surface of yeast, and screened for high affinity binders using a fluorescently labeled target. The high affinity binders may be conveniently selected and isolated using flow cytometry. See, e.g., Kieke et al., 2001, supra.

In addition to random mutagenesis techniques, site-directed mutational techniques may be employed in combination with molecular modeling studies aimed at predicting mutations that will increase stability and binding affinity of the interaction complex between bacterial membrane and a test chimera or component thereof.

General Nucleic Acid Methodology:

The anti-microbial chimeras of the invention, and libraries of variants thereof, may be generated using basic nucleic acid methodology routine in the field of recombinant genetics. Basic texts disclosing the general methods of obtaining and manipulating nucleic acids in this invention include Sambrook and Russell, *Molecular Cloning, a Laboratory Manual* (3rd ed. 2001) and *Current Protocols in Molecular Biology* (Ausubel et al., eds., John Wiley & Sons, Inc. 1994-1997, 2001 version)).

Typically, the nucleic acid sequences encoding the chimeras of the invention are generated using amplification techniques. Examples of techniques sufficient to direct persons of skill through in vitro amplification methods are found in Berger, Sambrook, and Ausubel, as well as Dieffenbach & Dveksler, *PCR Primers: A Laboratory Manual* (1995): Mullis et al., (1987); U.S. Pat. No. 4,683,202; *PCR Protocols A Guide to Methods and Applications* (Innis et al., eds) Academic Press Inc. San Diego, Calif. (1990); (Innis); Arnheim & Levinson (Oct. 1, 1990) C&EN 36-47; The Journal Of NIH Research, 1991, 3: 81-94; Kwoh et al., 1989, Proc. Natl. Acad. Sci. USA, 86: 1173; Guatelli et al., 1990, Proc. Natl. Acad. Sci. USA, 87, 1874; Lomell et al., 1989, J. Clin. Chem., 35: 1826; Landegren et al., 1988, Science, 241: 1077-1080; Van Brunt, 1990, Biotechnology, 8: 291-294; Wu and Wallace, 1989, Gene, 4: 560; and Barringer et al., 1990, Gene 89: 117.

Amplification techniques can typically be used to obtain a population of sequences, e.g., evolved variants of the SRD or lysis components of the chimeras. In generating a population of variants, it is often desirable to obtain amplicons that do not include the primer sequences from the amplification primers. This can be achieved by using primers that include restriction enzyme sites, such as Bpml, that cleave at a distance from the recognition sequence. Such a method is exemplified in U.S. patent application Ser. No. 10/167,634. The amplified population can then be introduced into a chimera construct, thereby generating a library of chimeras for biological activity screening.

Display Libraries:

Libraries of variant components or complete chimeras may be constructed using a number of different display systems. In cell or virus-based systems, the elements of the library can be displayed, for example, on the surface of a particle, e.g., a virus or cell and screened for the ability to interact with other molecules, e.g., a superantigen of interest. In vitro display systems can also be used, in which the library elements are linked to an agent that provides a mechanism for coupling the element to the nucleic acid sequence that encodes it. These technologies include ribosome display and mRNA display.

As noted above, in some instances, for example, ribosomal display, a chimera variant is linked to the nucleic acid sequence through a physical interaction, for example, with a ribosome. In other embodiments, e.g., mRNA display, the chimera may be joined to another molecule via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similar linking group. Other near neutral amino acids, such as Ser can also be used in the linker sequence. Amino acid sequences which may be usefully employed as linkers include those disclosed in Maratea et al., 1985, Gene 40:39-46; Murphy et al., 1986, Proc. Natl. Acad. Sci. USA 83:8258-8262; U.S. Pat. Nos. 4,935,233 and 4,751,180. The linker sequence may generally be from 1 to about 50 amino acids in length, e.g., 2, 3, 4, 6, or 10 amino acids in length, but can be 100 or 200 amino acids in length.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Phage display technology may also be used for generating and screening libraries of chimeras or components thereof. Construction of phage display libraries exploits the bacteriophage's ability to display peptides and proteins on their surfaces, i.e., on their capsids. Often, filamentous phage such as M13, fd, or f1 are used. Filamentous phage contain single-stranded DNA surrounded by multiple copies of genes encoding major and minor coat proteins, e.g., pill. Coat proteins are displayed on the capsid's outer surface. DNA sequences inserted in-frame with capsid protein genes are co-transcribed to generate fusion proteins or protein fragments displayed on the phage surface. Phage libraries thus can display peptides representative of the diversity of the inserted sequences. Significantly, these peptides can be displayed in "natural" folded conformations. The fluorescent binding ligands expressed on phage display libraries can then bind target molecules, i.e., they can specifically interact with binding partner molecules such as antigens, e.g., (Petersen, 1995, Mol. Gen. Genet., 249:425-31), cell surface receptors (Kay, 1993, Gene 128:59-65), and extracellular and intracellular proteins (Gram, 1993, J. Immunol. Methods, 161:169-76).

The concept of using filamentous phages, such as M13 or fd, for displaying peptides on phage capsid surfaces was first introduced by Smith, 1985, Science 228:1315-1317. Peptides have been displayed on phage surfaces to identify many potential ligands (see, e.g., Cwirla, 1990, Proc. Natl. Acad. Sci. USA, 87:6378-6382). There are numerous systems and methods for generating phage display libraries described in the scientific and patent literature, see, e.g., Sambrook and Russell, *Molecule Cloning: A Laboratory Manual,* 3rd edition, Cold Spring Harbor Laboratory Press, Chapter 18, 2001; Phage, *Display of Peptides and Proteins: A Laboratory Manual*, Academic Press, San Diego, 1996; Crameri, 1994, Eur. J. Biochem. 226:53-58; de Kruif, 1995, Proc. Natl. Acad. Sci. USA, 92:393842; McGregor, 1996, Mol. Biotechnol., 6:155-162; Jacobsson, 1996, Biotechniques, 20:1070-1076; Jespers, 1996, Gene, 173:179-181; Jacobsson, 1997, Microbiol Res., 152:121-128; Fack, 1997, J. Immunol. Methods, 206:43-52; Rossenu, 1997, J. Protein Chem., 16:499-503; Katz, 1997, Annu. Rev. Biophys. Biomol. Struct., 26:27-45; Rader, 1997, Curr. Opin. Biotechnol., 8:503-508; Griffiths, 1998, Curr. Opin. Biotechnol., 9:102-108.

Typically, exogenous nucleic acids encoding the protein sequences to be displayed are inserted into a coat protein gene, e.g. gene III or gene VIII of the phage. The resultant fusion proteins are displayed on the surface of the capsid. Protein VIII is present in approximately 2700 copies per phage, compared to 3 to 5 copies for protein III (Jacobsson, 1996, supra). Multivalent expression vectors, such as phagemids, can be used for manipulation of the nucleic acid sequences encoding the fluorescent binding library and production of phage particles in bacteria (see, e.g., Felici, 1991, J. Mol. Biol., 222:301-310).

Phagemid vectors are often employed for constructing the phage library. These vectors include the origin of DNA replication from the genome of a single-stranded filamentous bacteriophage, e.g., M13 or f1 and require the supply of the other phage proteins to create a phage. This is usually supplied by a helper phage which is less efficient at being packaged into phage particles. A phagemid can be used in the same way as an orthodox plasmid vector, but can also be used to produce filamentous bacteriophage particle that contain single-stranded copies of cloned segments of DNA.

The displayed protein does not need to be a fusion protein. For example, a chimera or component thereof may attach to a coat protein by virtue of a non-covalent interaction, e.g., a coiled coil binding interaction, such as jun/fos binding, or a covalent interaction mediated by cysteines (see, e.g., Crameri et al., 1994, Eur. J. Biochem., 226:53-58) with or without additional non-covalent interactions. Morphosys have described a display system in which one cysteine is put at the C terminus of the scFv or Fab, and another is put at the N terminus of g3p (MorphoSys; Munich, Germany). The two assemble in the periplasm and display occurs without a fusion gene or protein.

The coat protein need not endogenous. For example, DNA binding proteins can be incorporated into the phage/phagemid genome (see, e.g., McGregor & Robins, 2001, Anal. Biochem., 294:108-117,). When the sequence recognized by such proteins is also present in the genome, the DNA binding protein becomes incorporated into the phage/phagemid. This can serve as a display vector protein. In some cases it has been shown that incorporation of DNA binding proteins into the phage coat can occur independently of the presence of the recognized DNA signal.

Other phage can also be used. For example, T7 vectors, T4 vector, T2 vectors, or lambda vectors can be employed in which the displayed product on the mature phage particle is released by cell lysis.

Another methodology is selectively infective phage (SIP) technology, which provides for the in vivo selection of interacting protein-ligand pairs. A "selectively infective phage" consists of two independent components. For example, a recombinant filamentous phage particle is made non-infective by replacing its N-terminal domains of gene 3 protein (g3p) with a protein of interest, e.g., an antigen. The nucleic acid encoding the antigen can be inserted such that it will be expressed. The second component is an "adapter" molecule in which the fluorescent ligand is linked to those N-terminal domains of g3p that are missing from the phage particle. Infectivity is restored when the displayed protein (e.g., a fluorescent binding ligand) binds to the antigen. This interaction attaches the missing N-terminal domains of g3p to the phage display particle. Phage propagation becomes strictly dependent on the protein-ligand interaction. See, e.g., Spada, 1997, J. Biol. Chem. 378:445-456; Pedrazzi, 1997, FEBS Lett. 415:289-293; Hennecke, 1998, Protein Eng. 11:405-410.

In addition to phage display libraries, analogous epitope display libraries can also be used. For example, the methods of the invention can also use yeast surface displayed libraries (see, e.g., Boder, 1997, Nat. Biotechnol., 15:553-557 and Feldhaus et al., 2003, Nat. Biotechnol., 21, 163-170), which can be constructed using such vectors as the pYD1 yeast expression vector. Yeast display wherein a library of elements (e.g., a library of chimera random mutants) is expressed on the yeast cell surface as a fusion with the yeast Aga2p protein may be used in combination with flow cytometry sorting using a fluorescently labeled target SAG (Kieke et al., 2001, supra). See also, U.S. Pat. Nos. 6,300,065 and 6,423,538.

In one embodiment, a yeast display system may be used to display and screen for variants with higher binding affinities, broader target specificity, etc. Other potential display systems include mammalian display vectors. The use of mammalian or other eukaryotic display systems are preferred so that post-translational modifications that may important in binding or affinity or membrane invasion activity are present in the expression products.

In vitro display library formats known to those of skill in the art can also be used, e.g., ribosome displays libraries and mRNA display libraries. In these in vitro selection technologies, proteins are made using cell-free translation and physically linked to their encoding mRNA after in vitro translation. In typical methodology for generating these libraries, DNA encoding the sequences to be selected are transcribed in vitro and translated in a cell-free system.

In ribosome display libraries (see, e.g., Mattheakis et al., 1994, Proc. Natl. Acad. Sci USA 91:9022-9026; Hanes & Pluckthrun, 1997, Proc. Natl. Acad. Sci USA, 94: 4937-4942) the link between the mRNA encoding the chimera and the chimera is the ribosome itself. The DNA construct is designed so that no stop codon is included in the transcribed mRNA. Thus, the translating ribosome stalls at the end of the mRNA and the encoded protein is not released. The encoded protein can fold into its correct structure while attached to the ribosome. The complex of mRNA, ribosome and protein is then directly used for selection against an immobilized target. The mRNA from bound ribosomal complexes is recovered by dissociation of the complexes with EDTA and amplified by RT-PCR.

Methods and libraries based on mRNA display technology, also referred to herein as puromycin display, are described, for example in U.S. Pat. Nos. 6,261,804; 6,281,223; 6207446; and 6,214553. In this technology, a DNA linker attached to puromycin is first fused to the 3' end of mRNA. The protein is then translated in vitro and the ribosome stalls at the RNA-DNA junction. The puromycin, which mimics aminoacyl tRNA, enters the ribosomal A site and accepts the nascent polypeptide. The translated protein is thus covalently linked to its encoding mRNA. The fused molecules can then be purified and screened for binding activity. The nucleic acid sequences encoding ligands with binding activity can then be obtained, for example, using RT-PCR. The chimeras or components thereof and sequences, e.g., DNA linker for conjugation to puromycin, can be joined by methods well known to those of skill in the art and are described, for example, in U.S. Pat. Nos. 6,261,804; 6,281,223; 6207446; and 6,214553.

Other technologies involve the use of viral proteins (e.g., protein A) that covalently attach themselves to the genes that encodes them. Fusion proteins are created that join the chimera or component thereof to the protein A sequence, thereby providing a mechanism to attach the chimeras or components thereof to the genes encoding them.

Plasmid display systems rely on the fusion of displayed proteins to DNA binding proteins, such as the lac repressor (see, e.g., Gates et al., 1996, J. Mol. Biol., 255:373-386; 1996, Methods Enzymol. 267:171-191). When the lac operator is present in the plasmid as well, the DNA binding protein binds to it and can be co-purified with the plasmid. Libraries can be created linked to the DNA binding protein, and screened upon lysis of the bacteria. The desired plasmid/proteins are rescued by transfection, or amplification.

Library Screening:

Methods of screening libraries of chimeras or components thereof are also well known in the art. Such libraries are typically screened using the target bacterial pathogen, or targeted membrane components (the "target"). The target may be attached to a solid surface or a specific tag, such as biotin. The target is incubated with a library of a chimera or a component thereof (i.e., random mutants of the SDR). Those polypeptides that bind to the target are then separated from those that do not using any of a number of different methods. These methods involve washing steps, followed by elution steps. Washing can be done, for example, with PBS, or detergent-containing buffers. Elution can be performed with a number of agents, depending on the type of library. For example, an acid, a base, or a protease can be used when the library is a phage display library. Selected clones may be subjected to further screening and individual clones evaluated for target binding profiles, binding affinities, and/or antimicrobial activity.

To facilitate the identification and isolation of the target-bound chimera or component thereof, the chimera or component thereof may also be engineered as a fusion protein to include selection markers (e.g., epitope tags). Antibodies reactive with the selection tags present in the fusion proteins or moieties that bind to the labels can then be used to isolate the complex via the epitope or label. For example, SRD-target complexes can be separated from non-complexed display targets using antibodies specific for the antibody selection "tag" e.g., an SV5 antibody specific to an SV5 tag.

Other detection and purification facilitating domains include, e.g., metal chelating peptides such as polyhistidine tracts (HIS tags) and histidine-tryptophan modules that allow purification on immobilized metals, protein A domains that allow purification on immobilized immunoglobulin, or the domain utilized in the FLAG extension/affinity purification system (Immunex Corp, Seattle Wash.). Any epitope with a corresponding high affinity antibody can be used, e.g., a myc tag (see, e.g., Kieke, 1997, Protein Eng. 10:1303-1310), V5 (Invitrogen), or an E-tag (Pharmacia). See also Maier, 1998, Anal. Biochem. 259:68-73; Muller, 1998, Anal. Biochem. 259:54-61.

The inclusion of a cleavable linker sequences such as Factor Xa, tobacco etch virus protease or enterokinase (Invitrogen, San Diego Calif.) between the purification domain and binding site may be useful to facilitate purification. For example, an expression vector of the invention may include a polypeptide-encoding nucleic acid sequence linked to six consecutive histidine residues. These residues bind with high affinity to metal ions immobilized on chelating resins even in the presence of denaturing agents and can be mildly eluted with imidazole.

Selection tags can also make the epitope or binding partner detectable or easily isolated by incorporation of, e.g., predetermined polypeptide epitopes recognized by a secondary reporter/binding molecule, e.g., leucine zipper pair sequences; binding sites for secondary antibodies; transcriptional activator polypeptides; and other selection tag binding compositions. See also, e.g., Williams, 1995, Biochemistry, 34:1787-1797.

Typical screening protocols employ multiple rounds of selection to identify a clone with the desired properties. For example, it may be desirable to select a chimera or component thereof with a binding avidity for a specified bacterial membrane target. Selection may be employed to isolate high affinity binders, using increasingly stringent binding conditions can be used to select chimeras or an SRD component thereof that bind to a target bacteria at increasingly greater binding affinities. A variety of other parameters can also be adjusted to select for high affinity SRD, e.g., increasing salt concentration, temperature, and the like.

Expression Systems:

The chimera of the invention may be produced using any of a number of systems to obtain the desired quantities of the protein. There are many expression systems well know in the art. (See, e.g., *Gene Expression Systems*, Fernandes and Hoeffler, Eds. Academic Press, 1999; Ausubel, supra.) Typically, the polynucleotide that encodes the chimera or component thereof is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs". Accordingly, the nucleic acids that encode the joined polypeptides are incorporated for high level expression in a desired host cell.

The production of CHAMPs as secreted proteins in plant, insect and mammalian expression systems is generally preferred, since the active components of the chimera will typically require various post-translational modifications to produce correctly-folded, biologically active polypeptides. In particular, given that defensins contain up to four disulfide bridges that are required for functional activity, and SRDs may contain glycosylation sites and disulfide bonds, expression of SRD/defensin chimeras as secreted proteins is preferred in order to take advantage of the robust structural integrity rendered by these post-translational modifications.

For example, insect cells possess a compartmentalized secretory pathway in which newly synthesized proteins that bear an N-terminal signal sequence transit from the endoplasmic reticulum (ER), to the Golgi apparatus, and finally to the cell surface via vesicular intermediates. The compartments of the secretory pathway contain specialized environments that enhance the ability of proteins that pass through to fold correctly and assume a stable conformation. For example, the ER supports an oxidizing environment that catalyzes disulfide bond formation, and both the ER and Golgi apparatus contains glycosylation enzymes that link oligosaccharide chains to secretory proteins to impart stability and solubility. In general, secreted proteins receive these modifications as a way of stabilizing protein structure in the harsher environment of the cell surface, in the presence of extracellular proteases and pH changes. One example of an insect expression system that may be used to express the chimeras of the invention is a Bacculovirus expression system (see below). The use of a Bacculovirus expression system to express a prototype SRD/defensin chimera is illustrated in Example 3, infra.

To illustrate, chimeras may be expressed in a Baculovirus system as follows. Briefly, DNA expressing a chimera are cloned into a modified form of the Baculovirus transfer vector pAcGP67B (Pharmingen, San Diego, Calif.). This plasmid contains the signal sequence for gp67, an abundant envelope surface glycoprotein on *Autographa californica* nuclear polyhedrosis virus (AcNPV) that is essential for the entry of Baculovirus particles into target insect cells. Insertion of the chimera gene into this vector will yield expression of a gp67 signal peptide fusion to the chimera, under the control of the strong Baculovirus polyhedrin promoter. The signal peptide will direct the entire protein through the secretory pathway to the cell surface, where the signal peptide is cleaved off and the chimera protein can be purified from the cell supernatant.

The Baculovirus transfer vector pAcGP67B may be modified by inserting a myc epitope and 6×His tag at the 3' end of the multiple cloning region for identification and purification purposes (pAcGP67B-MH). Chimera genes inserted into pAcGP67B-MH may be co-transfected with Baculogold DNA into Sf21 cells using the Baculogold transfection kit (Pharmingen). Recombinant viruses formed by homologous recombination are amplified, and the protein purified from a final amplification in High Five cells (Invitrogen, Carlsbad, Calif.), derived from *Trichoplusia ni* egg cell homogenates.

High Five cells have been shown to be capable of expressing significantly higher levels of secreted recombinant proteins compared to Sf9 and Sf21 insect cells.

Various transgenic plant expression systems may also be utilized for the generation of the chimera proteins of the invention, including without limitation tobacco and potato plant systems (e.g., see Mason et al., 1996, Proc. Natl. Acad. Sci. USA 93: 5335-5340).

Optionally, a bioreactor may be employed, such as the CELLine 350 bioreactor (Integra Biosciences). This particular bioreactor provides for culturing the plant cells within a relatively low-volume, rectangular chamber (5 ml), bounded by an oxygen-permeable membrane on one side, and a protein-impermeable, 10 kD molecular weight cut-off membrane on the other side, separating the cell compartment from the larger (350 ml) nutrient medium reservoir. The use of such a bioreactor permits simple monitoring of protein concentrations in the cell chamber, as a function of time, and simple characterization of proteins secreted into the medium using SDS-PAGE. Thus, such bioreactors also facilitate the expression of heterologous proteins in plant expression systems. Various other bioreactor and suspension-culture systems may be employed. See, for example, Decendit et al., 1996, Biotechnol. Lett. 18: 659-662.

As is known in the art, different organisms preferentially utilize different codons for generating polypeptides. Such "codon usage" preferences may be used in the design of nucleic acid molecules encoding the chimeras of the invention in order to optimize expression in a particular host cell system.

Evaluation and Selection of Therapeutic Chimera:

In order to develop therapeutically effective, high-affinity, high-specificity anti-microbial chimeras of the invention, the iterative application of structural, cell and organismal models may be used to design candidate chimera, evaluate performance characteristics, and ultimately select chimera to be applied therapeutically.

Briefly, as an example of the application of this iterative selection scheme, the initial step involves the structural design of the chimera, as described supra. Chimera constructs may then be expressed in a number of different cell types using various expression vectors and methods well known in the art. Candidate chimera expressed in these systems may be evaluated in cell based models for their ability to destroy target bacteria (see, e.g., Example 2, infra). Finally, chimera demonstrating a killing effect may be evaluated in an appropriate models of infection. Using Pierce's disease as an example, chimera activity against the causative agent Xf may be evaluated for killing bacteria colonization in an insect vector (i.e., glassy-winged sharpshooter) or the target plant (i.e., grapevines).

Where the therapeutic application of the anti-microbial chimera is a plant disease caused by a bacteria (i.e., citrus variegated chlorosis in orange trees, Pierce's Disease in grapevines, both caused by Xf), the chimera may be expressed directly in a transgenic plant (orange, grapevine), and the transgenic plant challenged with Xf.

Treatment of Pierce's Disease:

The anti-*Xylella fastidiosa* chimeras of the invention may be used for the treatment of Pierce's Disease in grapevines. Candidate chimeras may be initially evaluated using cell survival assays capable of assessing Xf killing. Chimeras showing activity in such in vitro assay systems may be further evaluated in plant assay systems. Chimeras demonstrating Xf killing in these systems may be used for the therapeutic treatment of symtomatic or asymptomatic grapevines or for the prophylactic treatment of vines exposed to Xf or at risk of being exposed to Xf.

For therapeutic treatment, an anti-Xf chimera is administered to the affected plant in a manner that permits the chimera to gain access to the xylem, where Xf colonies are located. Accordingly, the chimera may be administered directly to the xylem system, for example, via microinjection into the plant (e.g., stem, petiole, trunk). In one embodiment, anti-Xf chimera composition is injected directly into an infected grapevine, in one embodiment via a plugged, approximately 0.5 cm hole drilled into the vine, through which a syringe containing the composition may be inserted to deliver the composition to the xylem.

In one embodiment, a method of treating Pierce's Disease in a *Vitus vinifera* plant infected with Xf, comprises spraying the *Vitus vinifera* plant with an adherent composition containing an anti-Xf chimera. Various adherent compositions are known, and typically are formulated in liquid for ease of application with a sprayer. Adherent powders or semi-liquids may also be employed. A related embodiment is a method of preventing the development of Pierce's Disease in a *Vitus vinifera* plant, and comprises spraying the *Vitus vinifera* plant with an adherent composition containing an anti-Xf chimera.

Alternatively, an expressible gene encoding the chimera may be introduced into a plant virus capable of infecting grapevine plants, and the recombinant virus used to infect the plant, resulting in the expression of the chimera in the plant. In such applications, the use of xylem secretory signals may be used to target the chimera product to the infected plant's xylem.

The chimera may also be administered to the plant via the root system, in order to achieve systemic administration and access to primary xylem chambers. Similarly, the chimera may be administered to vine trunks, directly into primary xylem chambers, in order to deliver the chimera to upstream xylem throughout the plant.

The treatment of Pierce's Disease using the chimeras of the invention may also target the insect vectors responsible for the spread of Pierce's Disease. In this aspect of the invention, anti-Xf chimeras are introduced into the insect vector itself, so that the chimera can kill the Xf colonies residing in the insect, thereby inhibiting the further spread of the pathogen. In one embodiment, plants susceptible to feeding by a Xf vector insect (e.g., glassy winged sharpshooter) are sprayed with a composition that comprises the chimera and a carrier capable of adhering to the surface of the vine plants. When the vector insect feeds upon the treated plant, some of the composition is both ingested by the insect and injected into the plant. In effect, the insect thereby mediates the injection of the composition into the plant's xylem sap as it feeds on the plant. Accordingly, the anti-microbial composition then has the opportunity to inhibit the development of Xf colonies in the newly infected plant by killing bacteria at the feeding insertion site. Additionally, the ingestion of the composition by the insect also provides an opportunity to target and kill Xf colonies residing inside the vector insect, thereby inhibiting further spread.

Variations of this approach are contemplated. For example, a composition comprising an anti-Xf chimera of the invention, an insect food source, and/or a biological or chemical insect attractant may be placed locally in regions at risk for, or known to be susceptible to, insect-vectored Xf (e.g., vineyards, groves). In one embodiment, such a composition comprises an anti-Xf chimera solubilized in a sucrose solution. In another embodiment, the anti-Xf composition may be solubilized or suspended in a sap or sap-containing solution, preferably using sap from the insect vector's natural food sources. The composition may be exposed to the insect vector in any number of ways, including for example by placing appropriate feeder vessels in susceptible vineyards, adjacent crop areas, inhabited groves or in breeding habitats. In this regard, the glassy-winged sharpshooter inhabits citrus and avocado groves and some woody ornamentals in unusually high numbers. At immediate risk are vineyards near citrus orchards.

In addition to the treatment of established Xf infections, diseases caused by Xf may be prevented or inhibited using the chimeras of the invention in a prophylactic treatment approach, using the same or similar methods as described above. In one approach, for example, plants which are not susceptible to Xf infection and/or Xf-caused disease, but which are used by Xf insect vectors to breed or feed, may be sprayed with a composition containing an anti-Xf chimera of the invention. Insect vectors feeding upon such plants, for example, will ingest the composition, which is then available to kill Xf present in the insect vector, thereby preventing the spread of new infections to susceptible or carrier plants.

Generation of Xf Resistent Transgenic Plants:

Genes encoding the anti-Xf chimeras of the invention may be introduced into grapevines using several types of transformation approaches developed for the generation of transgenic plants (see, for example, Szankowski et al., 2003 Plant Cell Rep. 22: 141-149). Standard transformation techniques, such as Agrobacterium-mediated transformation, particle bombardment, microinjection, and elecroporation may be utilized to construct stably-transformed transgenic plants (Hiatt et al., 1989, Nature 342: 76-78). In addition, recombinant viruses which infect grapevine plants may be used to express the heterologous chimera protein of interest during viral replication in the infected host (see, for example, Kumagai et al., 1993, Proc. Natl. Acad. Sci. USA 90: 427-430).

Figure 9:
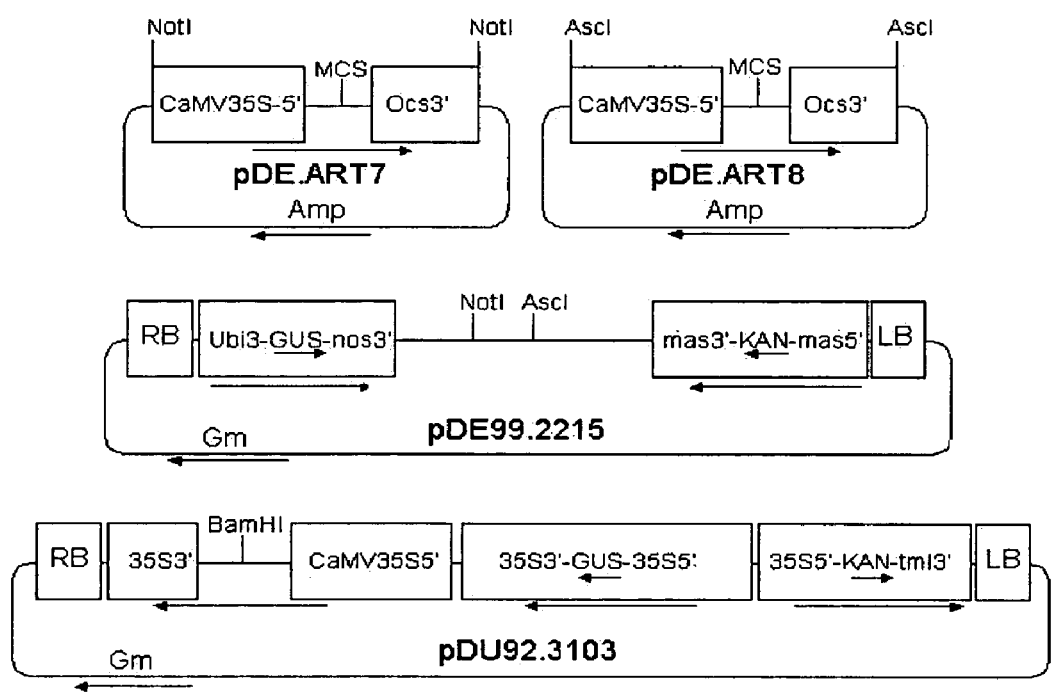
FIG. 9. Various exemplary vectors useful for development of transgenic plants expressing anti-Xf chimeras.

Vectors capable of facilitating the expression of a transgene in embryogenic cells of grapevine plants are known, several of which are shown in FIG. 9 by way of illustration, not limitation (see, for example, Verch et al., 2004, Cancer Immunol. Immunother. 53: 92-99; Verch et al., 1998, J. Immunol. Methods 220: 69-75; Mason et al., 1996, Proc. Natl. Acad. Sci. USA 93: 5335-5340). See, also, Szankowski et al., 2003, Plant Cell Rep. 22: 141-149.

As shown by the results of the study described in Example 4, supra, transgenic grape plants expressing a test protein in the plant's xylem can be generated using standard methodologies. In one embodiment, the genetic information necessary to express an anti-Xf chimera may be introduced into grapevine embryonic cells to generate transgenic grapevines expressing the chimera using standard transgenic methodologies. In preferred embodiments, DNA encoding the chimera is fused to a xylem targeting sequence or a secretion leader peptide from a xylem-expressed plant protein or precursor. In view of the success achieved with the test protein, pear PGIP (see Example 4, supra), a specific embodiment utilizes the PGIP secretion leader peptide:

```
MELKFSTFLSLTLLFSSVLNPALS.      (SEQ ID NO: 8)
```

Another example of a secretion leader which may be employed is the rice alpha-amylase leader:

```
MGKHHVTLCC VVFAVLCLAS SLAQA.   (SEQ ID NO: 9)
```

EXAMPLES

Example 1

Construction of Elastase-Cecropin and Elastase-Defensin Anti-Microbial Chimeras

DNAs encoding chimeric anti-microbial proteins comprising human neutrophil elastase fused to insect cecropin B via a polypeptide linker were prepared. More specifically, constructs linking the N-terminus of cecropin B to the C-terminus of elastase via a polypeptide linker were prepared, and have the amino acid sequences shown below.

Truncated HNE-Cecropin B; N- to C-terminus; linker peptide in boldface:

(SEQ ID NO: 4)
IVGGRRARPHAWPFMVSLQLRGGHFCGATLIAPNFVMSAAHCVANVNVRAVRVVLGAHNLSRR

EPTRQVFAVQRIFENGYDPVNLLNDIVILQLNGSATINANVQVAQLPAQGRRLGNGVQCLAMGW

GLLGRNRGIASVLQELNVTVVTSLCRRSNVCTLVRGRQAGVCFGDSGSPLVCNGLIHGIASFVR

GGCASGLYPDAFAPVAQFVNWIDSIIQRW KIFKKIEKMGRNIRDGIVKAGPAIEVLGSAKAIGK

In addition, constructs encoding chimeric anti-microbial proteins comprising human neutrophil elastase (N-terminal) fused to spinach group IV defensin (C-terminal) via the polypeptide linkers (GSTAPPA)$_2$ or GSTAPPAGSTA were also prepared, and have the amino acid sequences shown below (linkers shown in boldface).

(SEQ ID NO:6)
MTLGRRLACL FLACVLPALL LGGTALASEI VGGRRARPHA WPFMVSLQLR GGHFCGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTH GSTAPPAGSTAPPA GIFSSRKCKT PSKTFKGICT

RDSNCDTSCR YEGYPAGDCK GIRRRCMCSK PC (SEQ ID NO:7)
MTLGRRLACL FLACVLPALL LGGTALASEI VGGRRARPHA WPFMVSLQLR GGHFGGATLI

APNFVMSAAH CVANVNVRAV RVVLGAHNLS RREPTRQVFA VQRIFENGYD PVNLLNDIVI

LQLNGSATIN ANVQVAQLPA QGRRLGNGVQ CLAMGWGLLG RNRGIASVLQ ELNVTVVTSL

CRRSNVCTLV RGRQAGVCFG DSGSPLVCNG LIHGIASFVR GGCASGLYPD AFAPVAQFVN

WIDSIIQRSE DNPCPHPRDP DPASRTH GSTAPPAGSTA GIFSSRKCKT PSKTFKGICT

RDSNCDTSCR YEGYPAGDCK GIRRRCMCSK PC

Example 2

Anti-Microbial Activity of Cecropin and Neutrophil Elastase against *Xylella fastidiosa* and *E. Coli*

The anti-microbial activities of the active components of the chimera described in Example 1, infra, were evaluated in cell viability assays with both *Xylella fastidiosa* and *E. coli*. Xf strain "Stags Leap" and *E. coli* strain HB 101 were used. Briefly, cells were grown in liquid LB medium overnight (*E. coli*) or in solid PW medium (Almeida et al., 2004, Current Microbiol. 48: 368-372) for a week (Xf), centrifuged at 6500×g for 1 min and resuspended in 10 mM sodium phosphate buffer (pH 7.4) to give approximately $10^6$ colony forming units/ml.

Insect Cecropin B (5 μM) (Sigma) and Human Neutrophil Elastase (2.5 nM) (Sigma) were added to 0.25 ml of bacterial suspension and cells were incubated at 37 C. After 30 and 60 minutes, aliquots were subjected to serial dilutions, spread on LB or PW plates and incubated for 24 hours for *E. coli* and 1 week for Xf. Bacterial growth was monitored by counting the colony forming units (cfu) in the presence of cecropin B (5 μM), neutrophil elastase (2.5 nM), and cecropin B (5 μM) plus neutrophil elastase (2.5 nM), and in the absence of any inhibitor. Antibacterial activity was expressed as killing (%).

Figure 3:
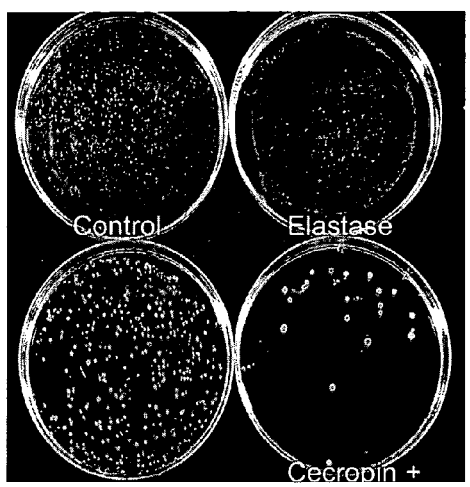
FIG. 3. Anti-microbial activity of cecropin B and human neutrophil elastase on Xf and *E. coli*. (A) anti-*Xylella fastidiosa* activities, (B) anti-*E. coli* activities. Xf was grown on PW plates for 1 week, and *E. coli* plates were grown for 24 hours, in the presence or absence of cecropin and elastase. See Example 2, infra.
Figure 3:
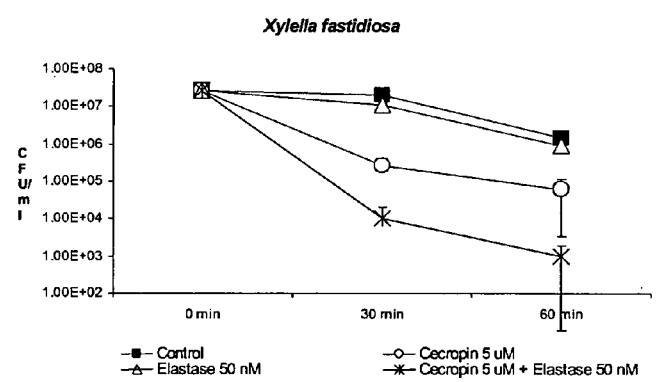
Figure 3:
Figure 3:
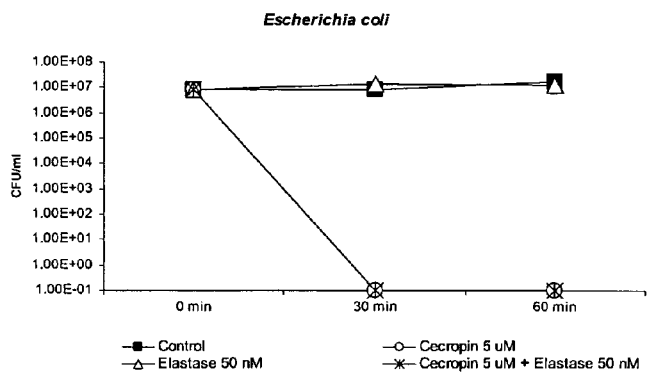

The results are presented in FIG. 3. Elastase alone was insufficient to inhibit bacterial growth. Cecropin B demonstrated some growth inhibition against Xf, and complete growth inhibition of *E. coli* after 30 minutes (FIG. 3). However, the combination of cecropin B and elastase resulted in a synergistic growth inhibitory effect against Xf (FIG. 3A).

Example 3

Expression of SRD-Defensin Chimera in Insect Cell System

A prototype SRD-defensin chimera, comprising rat mannose binding protein (as the SRD) linked to a mammalian beta-defensin, was expressed in a Baculovirus expression system. The chimera SRD and defensin components are linked via a polypeptide linker with the amino acid sequence QASHTCVCEFNCAPL. The chimera has the following structure (where the SRD component is underlined, the linker is in bold type, and the defensin component is in italics):

(SEQ ID NO:10)
LCKKFFVTNR ERMPFSRCRK LCSELRGTVA IPRNAEENKA IQEVAGHKRE NHWKSAFLGI

TDEVTEGQFM YVTGGRLTYS NWKKDEPNDH GSGEDCVTIV DNGLWNDISC QASHTCVCEF

NCAPLSCGRN GGVCIPIRCP VPMRQIGTCF GRPVKCCRSW

Figure 4:
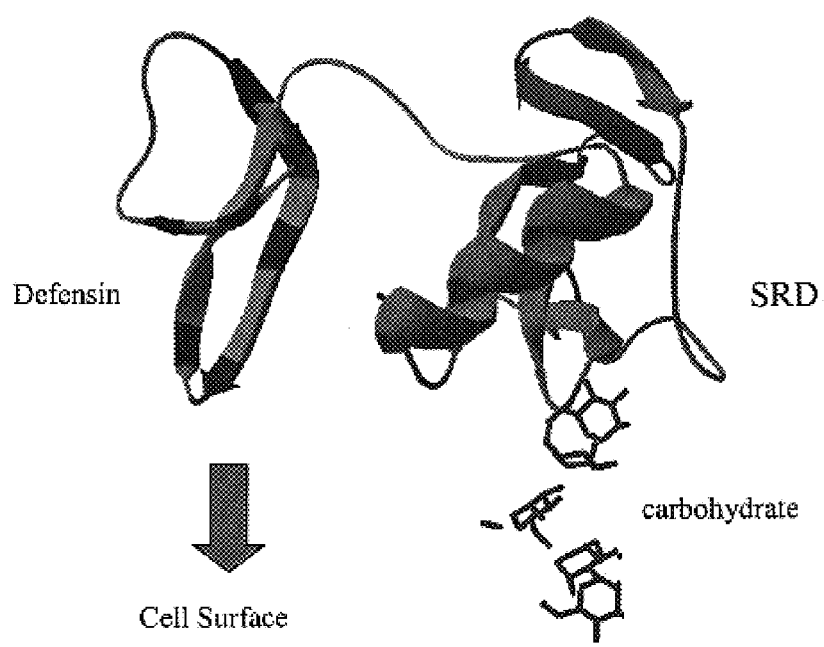
FIG. 4. Molecular model of an SRD-Defensin chimera. The membrane-permeable defensin and the mannose-binding loop are both oriented toward the bacterial membrane. The SRD (a rat mannose binding domain) attachment to mannose also allows membrane insertion of defensin.

A molecular model of the chimera is shown in FIG. 4. The membrane-permeable defensin and the mannose-binding loop are both pointed toward the bacterial membrane. The SRD (a mannose binding domain) attachment to mannose also allows membrane insertion of defensin.

Figure 5:
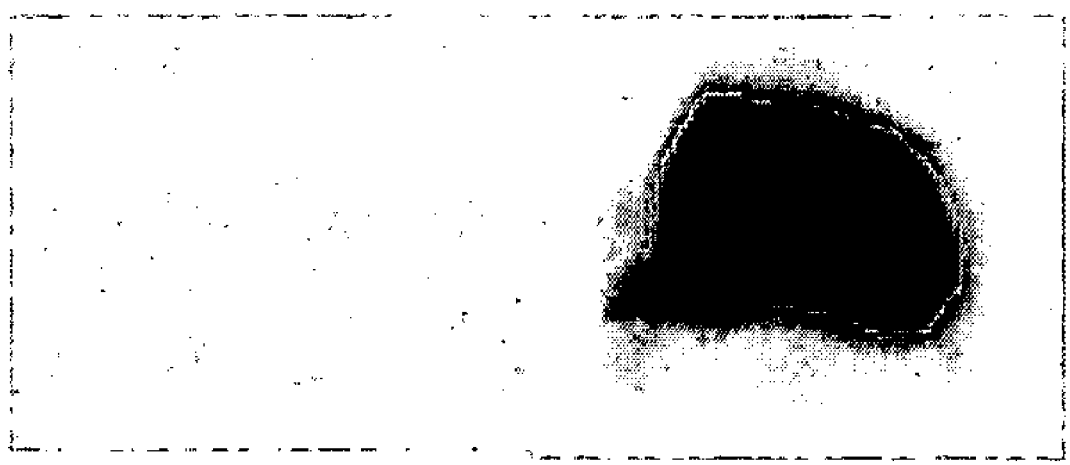
FIG. 5. Expression of a prototype SRD/defensin chimera protein in insect cells using Baculovirus expression vector (see Example 3, infra). Lysates from control (lane 1) and chimera-infected (lane 2) insect cells were analyzed by Western blot using anti-myc antibody.

For expression in the insect cell system, DNA encoding the chimera was cloned into a modified form of the Baculovirus transfer vector pAcGP67B (Pharmingen, San Diego, Calif.). Plasmid pAcGP67B was further modified by inserting a myc epitope and 6×His tag at the 3' end of the multiple cloning regions for Western blot identification and purification purposes, respectively (pAcGP67B-MH). Chimera genes inserted into pAcGP67B-MH were co-transfected with Baculogold DNA into Sf21 cells using the Baculogold transfection kit (Pharmingen). Recombinant viruses formed by homologous recombination were amplified, and the protein was purified from a final amplification in High Five cells (Invitrogen, Carlsbad, Calif.), derived from *Trichoplusia ni* egg cell homogenates. Recombinant chimera was successfully expressed using this system (see FIG. 5).

Example 4

Generation of Transgenic Grape Plants Expressing Pear Polygalacturanase

Figure 6:
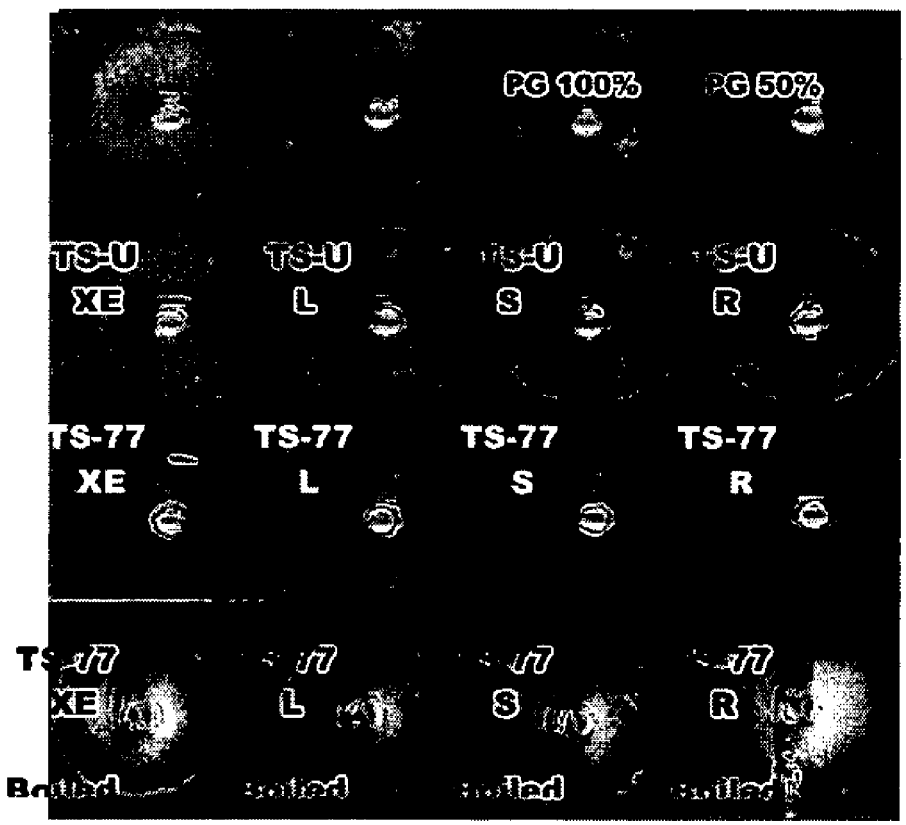
FIG. 6. Expression of pear PGIP in xylem exudate and in different organs of Thompson Seedless transgenic line 77 plants. (A) Total protein (10 µg) from xylem exudates (XE) and 1 M NaCl, 0.1 M NaAcetate pH 5 extraction of cell walls from leaves (L), stems (S) and roots (R) from an untransformed control (TS-U) and transgenic line 77 (TS-77) analyzed with antibodies to deglycosylated pear PGIP. (B) The inhibition of the endo-PG activity from culture filtrates of *B. cinerea* was determined by radial diffusion assay in agarose on the same samples.
Figure 7:
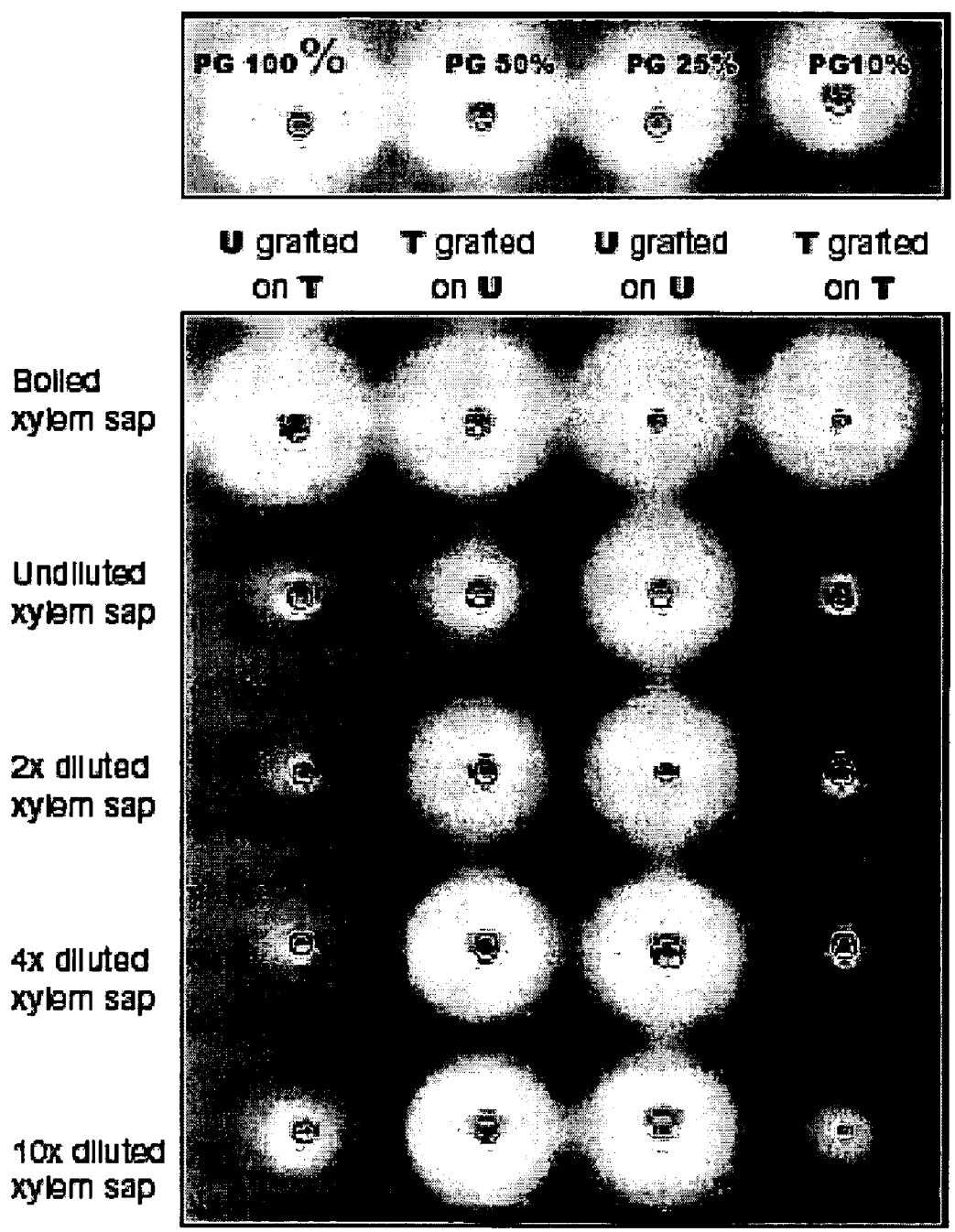
FIG. 7. PGIP activity in the xylem sap of different graft combinations. First row corresponds to 100, 50, 25 and 10% PG dilutions. Second row corresponds to boiled samples, and the rest of the rows correspond to different dilutions of xylem sap. U and T are Thompson Seedless untransformed and transgenic line 77 respectively.
Figure 8:
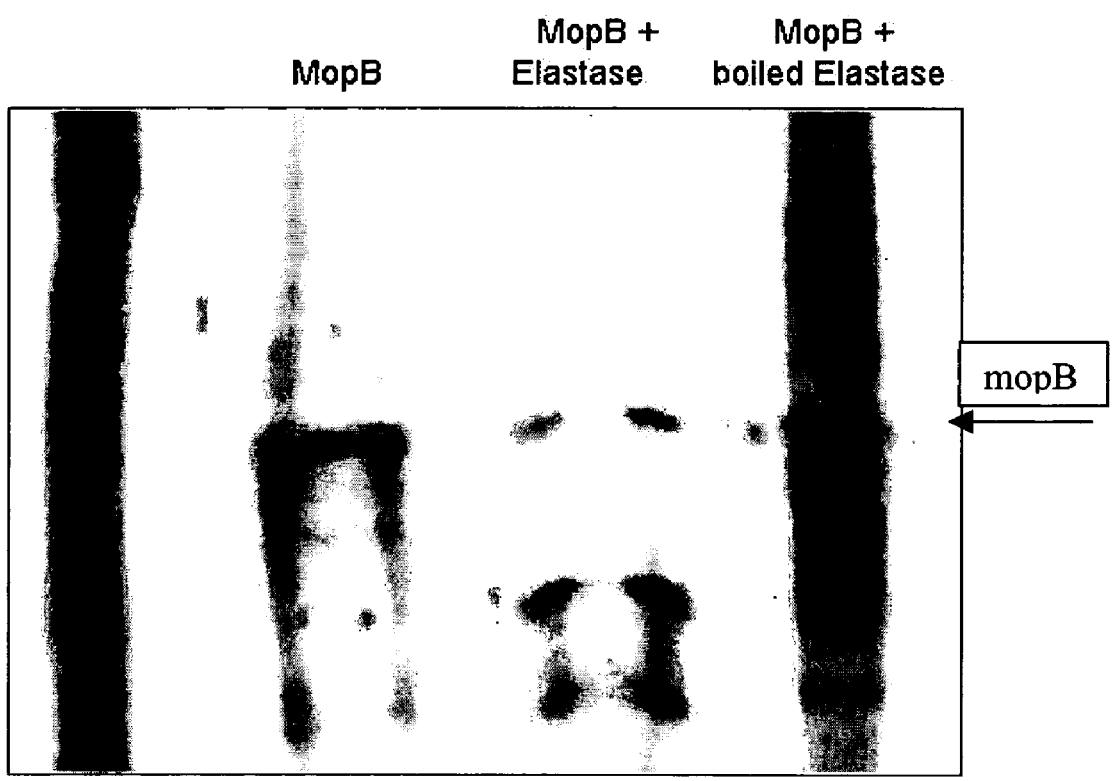
FIG. 8. Human neutrophil elastase digestion of Xf outer-membrane protein mopB. 1 µg purified mopB (D. Breuning, University of California, Davis) was incubated with approximately 0.02 units of human neutrophil elastase (Sigma) for 1 hour and then subjected to SDS-PAGE. Boiled HNE was incubated with mopB as a negative control.

Transgenic grape plants expressing pear polygalacturanase inhibiting protein (PGIP) were generated as described (Meredith et al., 2003, Proceedings of the 2003 Pierce's Disease Research Symposium, Calif. Dept. Food & Agriculture, p. 23-25). Briefly, pre-embryogenic calluses taken from anthers of *Vitis vinifera* "Thomson Seedless" and "Chardonnay" varietals were cultivated with *Agrobacterium tumifaciens* harboring a plasmid encoding the pear PGIP gene under the control of the CaMV $^{35}$S promoter. Correctly-folded, biologically active PGIP was expressed in the leaves, roots, stems and xylem sap of the resulting transgenic plants (see FIGS. 6 and 7).

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

---

What is claimed is:

1. A chimeric anti-microbial protein comprising a surface recognition domain physically linked to an insect cecropin B, wherein the surface recognition domain is capable of binding to a component of the cell membrane of *Xylella fastidiosa* and is human neutrophil elastase or an active fragment thereof, and wherein the C-terminus of the surface recognition domain is physically linked to the N-terminus of insect cecropin B by a fused polypeptide linker of between 2 and 20 amino acid residues.

2. The chimeric anti-microbial protein of claim 1, which anti-microbial protein has an amino acid sequence selected from the group consisting of SEQ ID NO: 4 and SEQ ID NO: 5.

3. An isolated nucleic acid molecule encoding a chimeric anti-microbial protein according to claim 2.

4. An expression vector comprising the nucleic acid molecule of claim 3.

5. A cell comprising the expression vector of claim 4.

6. A method of producing a chimeric anti-microbial protein comprising:

(a) providing an expression vector according to claim 4,
(b) transforming or transfecting a suitable host cell with the expression vector, and
(c) expressing the chimeric anti-microbial protein encoded by the expression vector.

7. An isolated nucleic acid molecule encoding a chimeric anti-microbial protein according to claim 1, the chimeric anti-microbial protein further containing a fused N-terminal xylem secretory leader.

8. An isolated nucleic acid molecule according to claim 7, wherein the N-terminal xylem secretory leader is selected from the group consisting of SEQ ID NO: 6 and SEQ ID NO: 7.

9. An expression vector comprising the nucleic acid molecule of claim 8.

10. A cell comprising the expression vector of claim 9.

11. A *Vitus vinifera* cell comprising the expression vector of claim 9.

12. A transgenic *Vitus vinifera* plant comprising the expression vector of claim 9.

13. A method of treating Pierce's Disease in a *Vitus vinifera* plant infected with Xf, comprising introducing a chimeric anti-microbial protein according to claim 1 into the xylem of the infected *Vitus vinifera* plant.

14. A method of treating Pierce's Disease in a *Vitus vinifera* plant infected with Xf, comprising contacting Xf cells present in the infected plant with a chimeric anti-microbial protein according to claim 1.

15. A method of treating Pierce's Disease in a *Vitus vinifera* plant infected with Xf, comprising spraying the *Vitus vinifera* plant with an adherent composition containing a chimeric anti-microbial protein according to claim 1.

16. A method of preventing the development of Pierce's Disease in a *Vitus vinifera* plant, comprising spraying the *Vitus vinifera* plant with an adherent composition containing a chimeric anti-microbial protein according to claim 1.

17. A method of inhibiting the spread of Pierce's Disease, comprising introducing a chimeric anti-microbial protein according to claim 1 into a glassy-winged sharpshooter insect vector of Xf.

18. The method according to claim 15, wherein the chimeric anti-microbial protein is introduced into the glassy-winged sharpshooter insect by feeding the insect a composition containing the chimeric anti-microbial protein.

\* \* \* \* \*

SEQUENCE LISTING

<160> NUMBER OF SEQ ID NOS: 10

<210> SEQ ID NO 1
<211> LENGTH: 219
<212> TYPE: PRT
<213> ORGANISM: Homo sapiens
<220> FEATURE:
<223> OTHER INFORMATION: truncated neutrophil elastase protein

<400> SEQUENCE: 1

```
Glu Ile Val Gly Gly Arg Arg Ala Arg Pro His Ala Trp Pro Phe Met
1               5                   10                  15

Val Ser Leu Gln Leu Arg Gly Gly His Phe Cys Gly Ala Thr Leu Ile
            20                  25                  30

Ala Pro Asn Phe Val Met Ser Ala Ala His Cys Val Ala Asn Val Asn
        35                  40                  45

Val Arg Ala Val Arg Val Val Leu Gly Ala His Asn Leu Ser Arg Arg
    50                  55                  60

Glu Pro Thr Arg Gln Val Phe Ala Val Gln Arg Ile Phe Glu Asn Gly
65                  70                  75                  80

Tyr Asp Pro Val Asn Leu Leu Asn Asp Ile Val Ile Leu Gln Leu Asn
                85                  90                  95

Gly Ser Ala Thr Ile Asn Ala Asn Val Gln Val Ala Gln Leu Pro Ala
            100                 105                 110
```

-continued

Gln Gly Arg Arg Leu Gly Asn Gly Val Gln Cys Leu Ala Met Gly Trp
           115                 120                 125

Gly Leu Leu Gly Arg Asn Arg Gly Ile Ala Ser Val Leu Gln Glu Leu
       130                 135                 140

Asn Val Thr Val Val Thr Ser Leu Cys Arg Arg Ser Asn Val Cys Thr
145                 150                 155                 160

Leu Val Arg Gly Arg Gln Ala Gly Val Cys Phe Gly Asp Ser Gly Ser
               165                 170                 175

Pro Leu Val Cys Asn Gly Leu Ile His Gly Ile Ala Ser Phe Val Arg
           180                 185                 190

Gly Gly Cys Ala Ser Gly Leu Tyr Pro Asp Ala Phe Ala Pro Val Ala
       195                 200                 205

Gln Phe Val Asn Trp Ile Asp Ser Ile Ile Gln
           210                 215

<210> SEQ ID NO 2
<211> LENGTH: 267
<212> TYPE: PRT
<213> ORGANISM: Homo sapiens

<400> SEQUENCE: 2

Met Thr Leu Gly Arg Arg Leu Ala Cys Leu Phe Leu Ala Cys Val Leu
1               5                   10                  15

Pro Ala Leu Leu Leu Gly Gly Thr Ala Leu Ala Ser Glu Ile Val Gly
            20                  25                  30

Gly Arg Arg Ala Arg Pro His Ala Trp Pro Phe Met Val Ser Leu Gln
        35                  40                  45

Leu Arg Gly Gly His Phe Cys Gly Ala Thr Leu Ile Ala Pro Asn Phe
    50                  55                  60

Val Met Ser Ala Ala His Cys Val Ala Asn Val Asn Val Arg Ala Val
65                  70                  75                  80

Arg Val Val Leu Gly Ala His Asn Leu Ser Arg Arg Glu Pro Thr Arg
                85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His

```
                260                 265

<210> SEQ ID NO 3
<211> LENGTH: 52
<212> TYPE: PRT
<213> ORGANISM: Spinachia oleracea

<400> SEQUENCE: 3

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Arg Cys Met Cys
        35                  40                  45

Ser Lys Pro Cys
    50

<210> SEQ ID NO 4
<211> LENGTH: 255
<212> TYPE: PRT
<213> ORGANISM: Artificial Sequence
<220> FEATURE:
<223> OTHER INFORMATION: Chimeric protein

<400> SEQUENCE: 4

Ile Val Gly Gly Arg Arg Ala Arg Pro His Ala Trp Pro Phe Met Val
1               5                   10                  15

Ser Leu Gln Leu Arg Gly Gly His Phe Cys Gly Ala Thr Leu Ile Ala
            20                  25                  30

Pro Asn Phe Val Met Ser Ala Ala His Cys Val Ala Asn Val Asn Val
        35                  40                  45

Arg Ala Val Arg Val Val Leu Gly Ala His Asn Leu Ser Arg Arg Glu
    50                  55                  60

Pro Thr Arg Gln Val Phe Ala Val Gln Arg Ile Phe Glu Asn Gly Tyr
65                  70                  75                  80

Asp Pro Val Asn Leu Leu Asn Asp Ile Val Ile Leu Gln Leu Asn Gly
                85                  90                  95

Ser Ala Thr Ile Asn Ala Asn Val Gln Val Ala Gln Leu Pro Ala Gln
            100                 105                 110

Gly Arg Arg Leu Gly Asn Gly Val Gln Cys Leu Ala Met Gly Trp Gly
        115                 120                 125

Leu Leu Gly Arg Asn Arg Gly Ile Ala Ser Val Leu Gln Glu Leu Asn
    130                 135                 140

Val Thr Val Val Thr Ser Leu Cys Arg Arg Ser Asn Val Cys Thr Leu
145                 150                 155                 160

Val Arg Gly Arg Gln Ala Gly Val Cys Phe Gly Asp Ser Gly Ser Pro
                165                 170                 175

Leu Val Cys Asn Gly Leu Ile His Gly Ile Ala Ser Phe Val Arg Gly
            180                 185                 190

Gly Cys Ala Ser Gly Leu Tyr Pro Asp Ala Phe Ala Pro Val Ala Gln
        195                 200                 205

Phe Val Asn Trp Ile Asp Ser Ile Ile Gln Arg Trp Lys Ile Phe Lys
    210                 215                 220

Lys Ile Glu Lys Met Gly Arg Asn Ile Arg Asp Gly Ile Val Lys Ala
225                 230                 235                 240

Gly Pro Ala Ile Glu Val Leu Gly Ser Ala Lys Ala Ile Gly Lys
                245                 250                 255
```

<210> SEQ ID NO 5
<211> LENGTH: 304
<212> TYPE: PRT
<213> ORGANISM: Artificial Sequence
<220> FEATURE:
<223> OTHER INFORMATION: Chimeric protein

<400> SEQUENCE: 5

```
Met Thr Leu Gly Arg Arg Leu Ala Cys Leu Phe Leu Ala Cys Val Leu
  1               5                   10                  15

Pro Ala Leu Leu Leu Gly Gly Thr Ala Leu Ala Ser Glu Ile Val Gly
             20                  25                  30

Gly Arg Arg Ala Arg Pro His Ala Trp Pro Phe Met Val Ser Leu Gln
         35                  40                  45

Leu Arg Gly Gly His Phe Cys Gly Ala Thr Leu Ile Ala Pro Asn Phe
     50                  55                  60

Val Met Ser Ala Ala His Cys Val Ala Asn Val Asn Val Arg Ala Val
 65                  70                  75                  80

Arg Val Val Leu Gly Ala His Asn Leu Ser Arg Arg Glu Pro Thr Arg
                 85                  90                  95

Gln Val Phe Ala Val Gln Arg Ile Phe Glu Asn Gly Tyr Asp Pro Val
            100                 105                 110

Asn Leu Leu Asn Asp Ile Val Ile Leu Gln Leu Asn Gly Ser Ala Thr
        115                 120                 125

Ile Asn Ala Asn Val Gln Val Ala Gln Leu Pro Ala Gln Gly Arg Arg
    130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
            180                 185                 190

Arg Gln Ala Gly Val Cys Phe Gly Asp Ser Gly Ser Pro Leu Val Cys
        195                 200                 205

Asn Gly Leu Ile His Gly Ile Ala Ser Phe Val Arg Gly Gly Cys Ala
    210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His Arg Trp Lys Ile Phe
            260                 265                 270

Lys Lys Ile Glu Lys Met Gly Arg Asn Ile Arg Asp Gly Ile Val Lys
        275                 280                 285

Ala Gly Pro Ala Ile Glu Val Leu Gly Ser Ala Lys Ala Ile Gly Lys
    290                 295                 300
```

<210> SEQ ID NO 6
<211> LENGTH: 333
<212> TYPE: PRT
<213> ORGANISM: Artificial Sequence
<220> FEATURE:
<223> OTHER INFORMATION: Chimeric protein

<400> SEQUENCE: 6

Met Thr Leu Gly Arg Arg Leu Ala Cys Leu Phe Leu Ala Cys Val Leu

```
              1               5                  10                 15
Pro Ala Leu Leu Leu Gly Gly Thr Ala Leu Ala Ser Glu Ile Val Gly
                20                  25                 30

Gly Arg Arg Ala Arg Pro His Ala Trp Pro Phe Met Val Ser Leu Gln
                35                  40                 45

Leu Arg Gly Gly His Phe Cys Gly Ala Thr Leu Ile Ala Pro Asn Phe
                50                  55                 60

Val Met Ser Ala Ala His Cys Val Ala Asn Val Asn Val Arg Ala Val
 65                 70                  75                 80

Arg Val Val Leu Gly Ala His Asn Leu Ser Arg Arg Glu Pro Thr Arg
                85                  90                 95

Gln Val Phe Ala Val Gln Arg Ile Phe Glu Asn Gly Tyr Asp Pro Val
                100                 105                110

Asn Leu Leu Asn Asp Ile Val Ile Leu Gln Leu Asn Gly Ser Ala Thr
                115                 120                125

Ile Asn Ala Asn Val Gln Val Ala Gln Leu Pro Ala Gln Gly Arg Arg
                130                 135                140

Leu Gly Asn Gly Val Gln Cys Leu Ala Met Gly Trp Gly Leu Leu Gly
145                 150                 155                160

Arg Asn Arg Gly Ile Ala Ser Val Leu Gln Glu Leu Asn Val Thr Val
                165                 170                175

Val Thr Ser Leu Cys Arg Arg Ser Asn Val Cys Thr Leu Val Arg Gly
                180                 185                190

Arg Gln Ala Gly Val Cys Phe Gly Asp Ser Gly Ser Pro Leu Val Cys
                195                 200                205

Asn Gly Leu Ile His Gly Ile Ala Ser Phe Val Arg Gly Gly Cys Ala
                210                 215                220

Ser Gly Leu Tyr Pro Asp Ala Phe Ala Pro Val Ala Gln Phe Val Asn
225                 230                 235                240

Trp Ile Asp Ser Ile Ile Gln Arg Ser Glu Asp Asn Pro Cys Pro His
                245                 250                255

Pro Arg Asp Pro Asp Pro Ala Ser Arg Thr His Gly Ser Thr Ala Pro
                260                 265                270

Pro Ala Gly Ser Thr Ala Pro Ala Gly Ile Phe Ser Ser Arg Lys
                275                 280                285

Cys Lys Thr Pro Ser Lys Thr Phe Lys Gly Ile Cys Thr Arg Asp Ser
                290                 295                300

Asn Cys Asp Thr Ser Cys Arg Tyr Glu Gly Tyr Pro Ala Gly Asp Cys
305                 310                 315                320

Lys Gly Ile Arg Arg Arg Cys Met Cys Ser Lys Pro Cys
                325                 330

<210> SEQ ID NO 7
<211> LENGTH: 330
<212> TYPE: PRT
<213> ORGANISM: Artificial Sequence
<220> FEATURE:
<223> OTHER INFORMATION: Chimeric protein

<400> SEQUENCE: 7

Met Thr Leu Gly Arg Arg Leu Ala Cys Leu Phe Leu Ala Cys Val Leu
 1               5                  10                 15

Pro Ala Leu Leu Leu Gly Gly Thr Ala Leu Ala Ser Glu Ile Val Gly
                20                  25                 30

Gly Arg Arg Ala Arg Pro His Ala Trp Pro Phe Met Val Ser Leu Gln
```

-continued

```
                35                  40                  45
Leu Arg Gly Gly His Phe Cys Gly Ala Thr Leu Ile Ala Pro Asn Phe
             50                  55                  60

Val Met Ser Ala Ala His Cys Val Ala Asn Val Asn Val Arg Ala Val
 65                  70                  75                  80

Arg Val Val Leu Gly Ala His Asn Leu Ser Arg Glu Pro Thr Arg
                 85                  90                  95

Gln Val Phe Ala Val Gln Arg Ile Phe Glu Asn Gly Tyr Asp Pro Val
                100                 105                 110

Asn Leu Leu Asn Asp Ile Val Ile Leu Gln Leu Asn Gly Ser Ala Thr
                115                 120                 125

Ile Asn Ala Asn Val Gln Val Ala Gln Leu Pro Ala Gln Gly Arg Arg
130                 135                 140

Leu Gly Asn Gly Val Gln Cys Leu Ala Met Gly Trp Gly Leu Leu Gly
145                 150                 155                 160

Arg Asn Arg Gly Ile Ala Ser Val Leu Gln Glu Leu Asn Val Thr Val
                165                 170                 175

Val Thr Ser Leu Cys Arg Arg Ser Asn Val Cys Thr Leu Val Arg Gly
                180                 185                 190

Arg Gln Ala Gly Val Cys Phe Gly Asp Ser Gly Ser Pro Leu Val Cys
                195                 200                 205

Asn Gly Leu Ile His Gly Ile Ala Ser Phe Val Arg Gly Gly Cys Ala
                210                 215                 220

Ser Gly Leu Tyr Pro Asp Ala Phe Ala Pro Val Ala Gln Phe Val Asn
225                 230                 235                 240

Trp Ile Asp Ser Ile Ile Gln Arg Ser Glu Asp Asn Pro Cys Pro His
                245                 250                 255

Pro Arg Asp Pro Asp Pro Ala Ser Arg Thr His Gly Ser Thr Ala Pro
                260                 265                 270

Pro Ala Gly Ser Thr Ala Gly Ile Phe Ser Ser Arg Lys Cys Lys Thr
                275                 280                 285

Pro Ser Lys Thr Phe Lys Gly Ile Cys Thr Arg Asp Ser Asn Cys Asp
                290                 295                 300

Thr Ser Cys Arg Tyr Glu Gly Tyr Pro Ala Gly Asp Cys Lys Gly Ile
305                 310                 315                 320

Arg Arg Arg Cys Met Cys Ser Lys Pro Cys
                325                 330

<210> SEQ ID NO 8
<211> LENGTH: 24
<212> TYPE: PRT
<213> ORGANISM: Pyrus communis
<220> FEATURE:
<223> OTHER INFORMATION: PGIP secretion leader peptide

<400> SEQUENCE: 8

Met Glu Leu Lys Phe Ser Thr Phe Leu Ser Leu Thr Leu Leu Phe Ser
1               5                   10                  15

Ser Val Leu Asn Pro Ala Leu Ser
            20

<210> SEQ ID NO 9
<211> LENGTH: 25
<212> TYPE: PRT
<213> ORGANISM: Oryzo sativa
<220> FEATURE:
<223> OTHER INFORMATION: alpha-amylase leader peptide
```

-continued

```
<400> SEQUENCE: 9

Met Gly Lys His His Val Thr Leu Cys Cys Val Val Phe Ala Val Leu
1               5                   10                  15

Cys Leu Ala Ser Ser Leu Ala Gln Ala
            20                  25

<210> SEQ ID NO 10
<211> LENGTH: 160
<212> TYPE: PRT
<213> ORGANISM: Artificial Sequence
<220> FEATURE:
<223> OTHER INFORMATION: Chimeric protein

<400> SEQUENCE: 10

Leu Cys Lys Lys Phe Phe Val Thr Asn Arg Glu Arg Met Pro Phe Ser
1               5                   10                  15

Arg Cys Arg Lys Leu Cys Ser Glu Leu Arg Gly Thr Val Ala Ile Pro
            20                  25                  30

Arg Asn Ala Glu Glu Asn Lys Ala Ile Gln Glu Val Ala Gly His Lys
        35                  40                  45

Arg Glu Asn His Trp Lys Ser Ala Phe Leu Gly Ile Thr Asp Glu Val
    50                  55                  60

Thr Glu Gly Gln Phe Met Tyr Val Thr Gly Gly Arg Leu Thr Tyr Ser
65                  70                  75                  80

Asn Trp Lys Lys Asp Glu Pro Asn Asp His Gly Ser Gly Glu Asp Cys
                85                  90                  95

Val Thr Ile Val Asp Asn Gly Leu Trp Asn Asp Ile Ser Cys Gln Ala
                100                 105                 110

Ser His Thr Cys Val Cys Glu Phe Asn Cys Ala Pro Leu Ser Cys Gly
            115                 120                 125

Arg Asn Gly Gly Val Cys Ile Pro Ile Arg Cys Pro Val Pro Met Arg
        130                 135                 140

Gln Ile Gly Thr Cys Phe Gly Arg Pro Val Lys Cys Cys Arg Ser Trp
145                 150                 155                 160
```